(12) United States Patent
Dahan et al.

(10) Patent No.: US 11,175,223 B2
(45) Date of Patent: Nov. 16, 2021

(54) IN-SITU MEASUREMENT OF NITRATE IN SOIL

(71) Applicant: B.G. NEGEV TECHNOLOGIES AND APPLICATIONS LTD., AT BEN-GURION UNIVERSITY, Beer-Sheva (IL)

(72) Inventors: Ofer Dahan, Midreshet Ben Gurion (IL); Shlomi Arnon, Lehavim (IL); Elad Yeshno, Midreshet Ben Gurion (IL)

(73) Assignee: B.G. NEGEV TECHNOLOGIES AND APPLICATIONS LTD., AT BEN-GURION UNIVERSITY, Beer-Sheva (IL)

( * ) Notice: Subject to any disclaimer, the term of this patent is extended or adjusted under 35 U.S.C. 154(b) by 0 days.

(21) Appl. No.: 16/466,128

(22) PCT Filed: Dec. 5, 2017

(86) PCT No.: PCT/IL2017/051318
§ 371 (c)(1),
(2) Date: Jun. 3, 2019

(87) PCT Pub. No.: WO2018/104939
PCT Pub. Date: Jun. 14, 2018

(65) Prior Publication Data
US 2020/0072737 A1    Mar. 5, 2020

Related U.S. Application Data

(60) Provisional application No. 62/429,884, filed on Dec. 5, 2016.

(51) Int. Cl.
*G01N 21/33* (2006.01)
*G01N 1/14* (2006.01)
(Continued)

(52) U.S. Cl.
CPC ............... *G01N 21/33* (2013.01); *G01N 1/14* (2013.01); *G01N 15/1436* (2013.01);
(Continued)

(58) Field of Classification Search
CPC ............... G01N 21/33; G01N 15/1436; G01N 2033/245; G01N 1/02; G01N 33/246
See application file for complete search history.

(56) References Cited

U.S. PATENT DOCUMENTS 7,927,883 B2    4/2011    Tuli et al.
8,381,582 B2    2/2013    Dahan
(Continued)

FOREIGN PATENT DOCUMENTS

DE    20 2015 000 747    6/2015
DE    20 2015 103 885    12/2016
(Continued)

OTHER PUBLICATIONS

Olp et al. U.S. Pub No. 2005/002030, Yukio Tachi, "Diffusion and sorption of Cs+, Na+, I- and HTO in compacted sodium montmorillonite as a function of porewater salinity: Integrated sorption and diffusion model", Jun. 7, 2013 (Year: 2013).*
(Continued)

*Primary Examiner* — Maurice C Smith
(74) *Attorney, Agent, or Firm* — Nixon & Vanderhye PC

(57) ABSTRACT

A system for measuring with the aid of light absorption spectrometry the concentration of one or more analytes in porewater in soil, the system comprising: one or more monitoring unit(s), each monitoring unit comprising a porewater sampler (1), an optical flow cell (2) with a tube connecting the liquid inlet port of said optical flow cell to said porewater sampler; and vacuum arrangement to enable extraction of porewater; at least one light source (5) for generating a light beam to be transmitted through said
(Continued)

optical flow cell (2); and at least one detector (8) for obtaining spectral information from the beam exiting said optical flow cell. A method of measurement is also provided.

19 Claims, 21 Drawing Sheets

(51) Int. Cl.
  *G01N 15/14* (2006.01)
  *G01N 33/24* (2006.01)
  *G01N 1/10* (2006.01)
(52) U.S. Cl.
  CPC ... *G01N 33/246* (2013.01); *G01N 2001/1031* (2013.01); *G01N 2201/08* (2013.01)

(56) References Cited

U.S. PATENT DOCUMENTS

| | | | |
|---|---|---|---|
| 9,714,901 | B2 | 7/2017 | Preiner et al. |
| 2003/0151744 | A1 | 8/2003 | Fernando et al. |
| 2005/0002030 | A1* | 1/2005 | Kolp .................. G01N 15/1475 356/335 |
| 2009/0038390 | A1 | 2/2009 | Dahan |
| 2009/0166520 | A1 | 7/2009 | Tuli et al. |
| 2010/0283993 | A1 | 11/2010 | Preiner et al. |

FOREIGN PATENT DOCUMENTS

| | | |
|---|---|---|
| JP | 10-160668 | 6/1998 |
| JP | 2001-349884 | 12/2001 |
| WO | 2014/127379 | 8/2014 |

OTHER PUBLICATIONS

Amber Hardison, "An Experimental Apparatus for Laboratory and Field-Based Perfusion of Sediment Porewater with Dissolved Tracers", Sep. 24, 2009 (Year: 2009).*
Dahan, O., et al., 2014, Nitrate leaching from intensive organic farms to groundwater. Hydrol. Earth Syst. Sci. 18(1): 333-341.
Shaw, B. D., et al., 2014, Analysis of ion and dissolved organic carbon interference on soil solution nitrate concentration measurements using UV absorption spectroscopy. Vadose Zone Journal.
Tuli, A., et al., 2009, In Situ Monitoring of Soil Solution Nitrate: Proof of Concept. Soil Sci Soc Am J 73, pp. 501-509.
Turkeltaub, T., et al., 2016, Real-time monitoring of nitrate transport in the deep vadose zone under a crop field—implications for groundwater protection. Hydrol. Earth Syst. Sci. 20(8): 3099-3108.
International Search Report for PCT/IL2017/051318, dated Mar. 27, 2018, 5 pages.
Written Opinion of the ISA for PCT/IL2017/051318, dated Mar. 27, 2018, 5 pages.
Shaw, B. D., et al., Analysis of ion and dissolved organic carbon interference on soil solution nitrate concentration measurements using ultraviolet absorption spectroscopy. Vadose Zone Journal, 2014, 13.12. Shaw, B. D., et al. Jan. 1, 2014 (Jan. 1, 2014).
Search Report issued in EP Appln. No. 17878499.7 dated Jun. 19, 2020.
Search Report issued in EP Appln. No. 17878499.7 dated Oct. 5, 2020.
Seeberg-Elverfeldt et al., "Rhizon sampling of porewaters near the sediment-water interface of aquatic systems" *Limnology and Oceanography: Methods*, vol. 3: 361-371 (2005).

* cited by examiner

IN-SITU MEASUREMENT OF NITRATE IN SOIL

CROSS-REFERENCES TO RELATED APPLICATIONS

This application is the U.S. national phase of International Application No. PCT/IL2017/051318 filed 5 Dec. 2017, which designated the U.S. and claims the benefit of U.S. Patent Application No. 62/429,884 filed 5 Dec. 2016, the entire contents of each of which are hereby incorporated by reference.

BACKGROUND AND SUMMARY

At present days detecting nitrate concentration in the soil or in deeper part of the unsaturated zone requires laboratory analysis of water samples which may be obtained from sediment extraction, suction lysimeters or water samples collected by a vadose zone monitoring system (abbreviated VMS; VMS is described in U.S. Pat. No. 8,381,582; Dahan, O., A. Babad, N. Lazarovitch, E. E. Russak, and D. Kurtzman. 2014. Nitrate leaching from intensive organic farms to groundwater. Hydrol. Earth Syst. Sci. 18(1): 333-341; Turkeltaub, T., D. Kurtzman, and O. Dahan. 2016. Real-time monitoring of nitrate transport in the deep vadose zone under a crop field—implications for groundwater protection. Hydrol. Earth Syst. Sci. 20(8): 3099-3108). Yet such processes require intensive field and laboratory labor which limits the required time resolution in tracking nitrate migration and transformation in the subsurface.

Ultraviolet (UV) absorption spectroscopy technique has been used to evaluate aqueous nitrate concentration for several decades. When UV light passes through a sample, the transmitted light interacts with the atoms and the molecules by scattering and absorption. Absorption will occur at different wavelengths, corresponding to the transition between energy levels. In the case of nitrate solution, UV light is being absorbed at wavelengths between 190 and 350 nm. Two distinct absorbance peaks can be observed: at 200 nm and 300 nm.

It has been reported that UV spectroscopy can be used for nitrate detection in soils, with the aid of fiber optics technology combined with suction cups (U.S. Pat. No. 7,927,883 and Tuli, A., Wei, J. B., Shaw, B. D., Hopmans, J. W., 2009. In Situ Monitoring of Soil Solution Nitrate: Proof of Concept. Soil Sci Soc Am J 73, pp. 501-509). UV absorption was measured in the aqueous phase of a porous cup installed in the soil, assuming chemical equilibrium with the soil solution. Hence, the accuracy of this method depends strongly on the time required to reach chemical equilibrium by diffusion processes between the inner part of the porous cup and the soil porewater. Since the chemical composition and nitrate concentration in agricultural soil porewater changes dynamically on time scale of hours due to irrigation pattern, plant nutrient uptake and microbial processes, delay caused by the time required for equilibrium to be achieved may result in significant differences between the measured solution in the cup to the actual chemical composition of the soil porewater. Indeed, it has been reported by the same research group that direct measurement in such porous cups is limited by the time required for equilibrium of the soil-cup solution and presence of dissolved organic carbon (abbreviated DOC; see Shaw, B. D., Wei, J. B., Tuli, A., Campbell, J., Parikhd, S. J., D, S. D., Buelow, M., Hopmans, J. W., 2014. Analysis of Ion and Dissolved Organic Carbon Interference on Soil Solution Nitrate Concentration Measurements Using Ultraviolet Absorption Spectroscopy. Vadose Zo. J. 13).

Measurement of nitrate concentration based on UV spectroscopy was also reported in U.S. Pat. No. 9,714,901, taking advantage of the wavelength range in the vicinity of the 200 nm absorption peak for nitrate detection. Concentration of nitrate is interpreted from soil water extract, where a soil sample is mixed with water. That is, the porewater is released to the soil extract solution creating a diluted solution of low nitrate concentration.

The present invention provides an elegant method of in-situ and real time measurement of nitrate in pore-water, eliminating the major drawbacks mentioned above, namely, the need to wait until chemical equilibrium is reached before a reliable absorbance reading can be obtained via direct measurement in a suction cup installed in the soil (see U.S. Pat. No. 7,927,883), and inaccuracies caused when analysis is done at a fixed, predetermined wavelength (see U.S. Pat. No. 9,714,901) that cannot encounter with changes occurring in concentration of nitrate in soil due to e.g., irrigation and fertilization.

One aspect of the invention is a method of quantitative in-situ and real time monitoring of one or more chemical species in pore-water of unsaturated zone (e.g., top soil, root zone and deep unsaturated zone, collectively simply named hereinafter "soil"), with the aid of light absorption spectrometry, the method comprising:

extracting porewater from soil using a porewater sampler (1), to produce a porewater stream;

directing said porewater stream into an in-line optical flow cell (2);

transmitting light beam across the porewater stream flowing through the optical flow cell (e.g., ultraviolet, visible or infrared light);

obtaining spectral information from the beam exiting the optical flow cell to determine the concentration of one or more analytes in the porewater with the aid of a first calibration curve constructed at a first selected wavelength suitable for the chemical composition of the soil and concentration range of said analyte; and switching to a second calibration curve constructed at a second wavelength when the concentration measured is not within said concentration range associated with said first calibration curve.

Another aspect of the invention is a system for measuring with the aid of light absorption spectrometry the concentration of one or more analytes in porewater, the system comprising:

one or more monitoring unit(s), each monitoring unit comprising a porewater sampler (1), an optical flow cell (2) with a tube connecting the liquid inlet port of said optical flow cell to said porewater sampler; and vacuum arrangement (3) enabling generation of low pressure (tension) within the porewater sampler;

at least one light source (5) for generating a light beam to be transmitted through said optical flow cell (2); and at least one detector (8) for obtaining spectral information from the beam exiting said optical flow cell.

Experimental results reported below (see Example 1 and FIGS. 1A, 1B, 1C and 2), based on continuous extraction of water from a periodically irrigated soil-packed column, into which nitrate solution was initially injected (water extraction was accomplished using a porewater sampler (1) with a suitable porous interface as described below), indicate good agreement between nitrate concentration calculated from UV light absorbance occurring when the extracted water flows in an optical flow cell (2) through which UV light beam is transmitted, and comparative methods. The experiment reported below lasted ten days, demonstrating that the method of the invention enables measuring porewater almost directly, to observe rapid changes which occur in soil through percolation events.

A battery consisting of a pore water sampler (1), an optical flow cell (2) and a vacuum arrangement (3), enabling generation of low pressure (tension) within the porewater sampler and achieving porewater stream from the soil through the porous interface to the optical flow cell, is referred to herein as 'monitoring unit'. Several alternatives may be considered for the vacuum arrangements. These may include a sampling cell charged with vacuum, peristaltic pump, vacuum pump, gravitational water column (syphon), and hanging cups. Especially preferred is vacuum arrangement based on a sampling cell charged with vacuum. That is, the method of the invention preferably includes a step of discharging the stream from the optical flow cell (2) to a sampling cell (3); the sampling cell thus serves two useful purposes simultaneously: generation of low pressure (tension) within the porewater sampler and collection of samples. Hereinafter reference is therefore made to the preferred monitoring unit consisting of a porewater sampler (1), an optical flow cell (2) and a sampling cell (3).

Accordingly, an especially preferred embodiment of the invention is a system for measuring, with the aid of light absorption spectrometry, the concentration of one or more analytes in porewater, the system comprising:

one or more monitoring unit(s), each monitoring unit consisting of a porewater sampler (1), an optical flow cell (2) and a sampling cell (3), with tubes connecting the liquid inlet and outlet ports of said optical flow cell to said porewater sampler and sampling cell, respectively;

a vacuum generating device in fluid communication with the sampling cell(s) to enable extraction of porewater;

at least one light source (5) for generating a light beam to be transmitted through said optical flow cell (2); and at least one detector (8) for obtaining spectral information from the beam exiting said optical flow cell.

DETAILED DESCRIPTION

In general, an array of monitoring units is installed in a field, as illustrated below, to enables real-time, continuous, in-situ data on absorption spectrum of soil porewater from multiple sampling points across a 3D measured domain (e.g. agricultural field or contaminated site during remediation operation) to be analyzed to create real-time 3D distribution map of selected chemical components, for example, continuous measurement variations of nitrate concentration in soil subjected to irrigation and fertilization. Hereinafter, the term "field" refers to any porous domain of variable water saturation degree. These may include the soil root zone, unsaturated zone, saturated parts of the subsurface, namely groundwater, or an array of individual or multiple growing pots.

One feature of the invention resides in operating the flow of the porewater, to ensure a continuous fresh stream of porewater from the porewater sampler to the optical flow cell. The extraction of porewater is accomplished using a small porewater sampler [e.g., inner volume ≤4 ml] connected using small diameter tubing [e.g., inner diameter ≤2.0 mm] to a small volume optical flow cell [e.g., inner volume ≤2 ml], to minimize the dead volume between the soil porewater and the analytical zone [e.g., less than 10 ml]. As such, the concentration of the analyte is measured continuously in a fresh stream of porewater. The method of the invention is preferably devoid of a step of diluting the porewater.

Another feature of the present invention resides in a smart selection of a suitable wavelength to achieve an efficient spectral analysis, and the ability to switch from one calibration curve to another in response to indications received from the spectral analysis. Experimental work conducted in support of this invention shows that quite often each particular field has its own typical 'chemical signature', namely, a composition of chemicals as dictated by the soil type, climate conditions, and agricultural regime, and therefore a unique typical absorption interference which obstructs the measurement of the analyte of interest. To overcome this problem, each field under consideration is associated with its own calibration equation measured at an optimal wavelength. Furthermore, since every monitoring unit is located in a different point in the soil across the field, and since the soil is also known to be a heterogeneous domain it is also possible that each and every monitoring unit will have its own chemical composition and therefore its own calibration equation.

Figure 3:
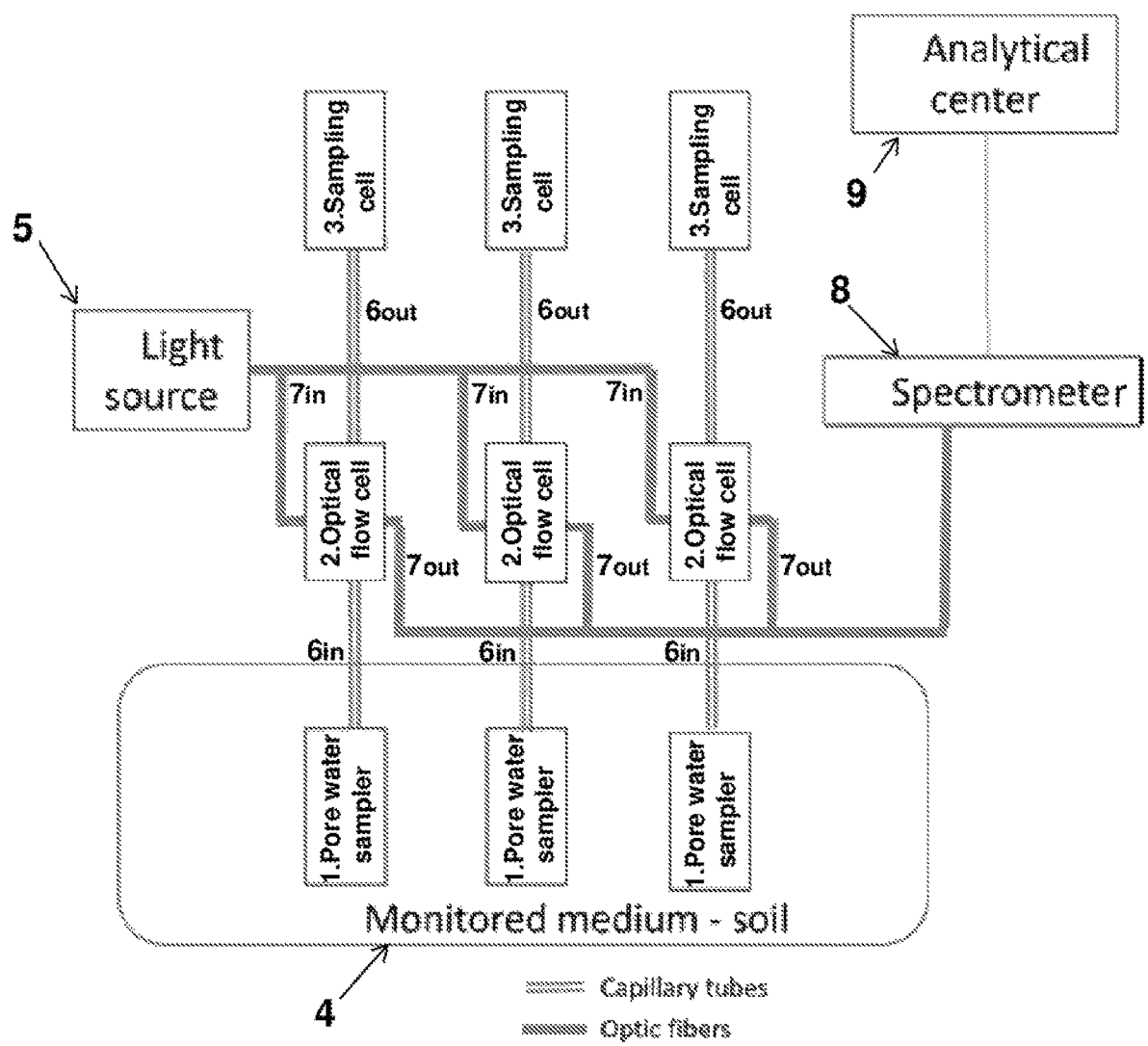
FIG. 3 illustrates a preferred embodiment of the system of the invention.

Reference is now made to FIG. 3, which illustrates a preferred embodiment of the system of the invention, showing an array of monitoring units installed at different locations across a field to create a network of sampling points in said field, wherein the system comprises a single light source and a single detector, adapted to carry out the method of the invention.

As shown in FIG. 3, a porewater sampler (1) is connected to an optical flow cell (2), which in turn is connected to a sampling cell (3), using small diameter tubing, e.g., capillary tubes (6), to provide an individual monitoring unit. It is seen that in the specific array illustrated in FIG. 3, three monitoring units are placed in the monitored medium—soil (4). Nevertheless, the number of monitoring units can be readily adjusted to meet different requirements. Light travels from a light source (5) through optic fibers (7) to each optical flow cell (2), from which the exiting beam propagates to the spectrometer (8). For example, in the embodiment shown in FIG. 3, an automated multiplexing robot can be used to shift the optical flow cell (2) from the light beam. As such a light window between the light source (5) and the spectrometer (8) is located in a constant position enabling mechanical shifting of the water in the different optical flow cells to be analyzed sequentially. Nevertheless other multiplexing devices may be used to either split or divert the light beam from the light source (5) to the different optical flow cells (2) and to the spectrometer (8). The analytical center, i.e., a computer (9) serves three main functions: (i) to control the operation of the light source, spectrometer, and multiplexing device while synchronizing measurements with the absorption data, (ii) determine concentration of specific chemical components on the basis of absorption spectrum, and (iii) create concentration distribution map of target chemical constituents in the monitored medium.

Turning now to each of the elements shown in FIG. 3 in more detail, it should be noted that porewater stream is generated under a very low flow-rate (from 1-5 ml per hour, depending on the soil hydraulic conditions). This can be achieved with the aid of porewater samplers provided with a suitable porous interface (1), e.g., made of ceramic, clay, borosilicate, porous plastic films, porous metals. For example, pore water sampler (1) can be a solid porous interface with no internal void. Alternatively, pore water sampler (1) preferably comprises an elongated body bounded by a porous lateral surface with a spacer disposed within the interior defined by said lateral surface, said spacer occupying at least 70% of the volume of said interior space, e.g., at least 90%. More specifically, the pore water sampler (1) comprises a porous interface in the form of a lateral surface of a cylinder; the internal space of the cylindrical surface is designed specifically to have a minimal inner dead volume, e.g., by co-axially placing therein a suitable spacer element occupying about 90-98% of said internal space, such that the porewater flows in the annular space between the inner walls of said cylindrical interface and the co-axially positioned spacer.

Figure 4:
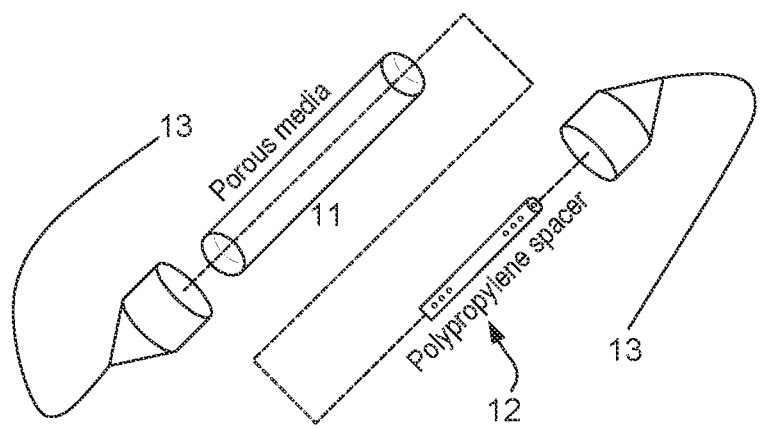
FIG. 4 illustrates a porewater sampler having an elongated cylindrical body.

For example, soil water is extracted according to the present invention using a porewater sampler having an elongated cylindrical body as illustrated in FIG. 4 (or alternatively, rectangular body). Its operation mechanism is similar to standard tensiometers or suction lysimeters. The porewater sampler of the invention comprises a porous ceramic pipe (11) (e.g., allowing air entry pressure of 1.5-2.0 bar). The dimensions of the porous interface, namely, length and outer diameter, are preferably in the ranges from 5 to 10 cm and 1 to 3 cm, respectively. The porous interface is capped from both sides to create a sealed cylindrical porous volume. To decrease the overall dead volume (the volume between the soil and optical flow cell) a spacer (12), e.g., a plastic (polypropylene) spacer is mounted in the interior of the porous pipe, to fill most of internal volume of the porous pipe. Optionally, the porewater sampler may be connected through the caps closing the open bases of the porous tube using additional small diameter tubing (13) to enable connection to pressure transduced or enable access for cleanup and maintenance of the porous interface through injection of liquid or gas which can flow through the entire setup, from the inner part of the porous interface through the optical flow cell to the sampling cell.

Turning now again to FIG. 3, the porewater stream is created under application of vacuum in the sampling cell (3) (generated by a regulated vacuum pump as explained in more detail below; in general the vacuum is set between 10 and 30 kPa). The porewater stream flows from porewater sampler (1) through small diameter tubing (6in), with inner diameter from 1.0 to 2.0 mm, e.g., around 1.5-1.8 mm, for example, capillary tube made of chemically resistant plastic, preferably low density polyethylene (commercially available from Freeling Wade) to a small volume optical flow cell (2), which discharges the stream to sampling cell (3).

Figure 5:
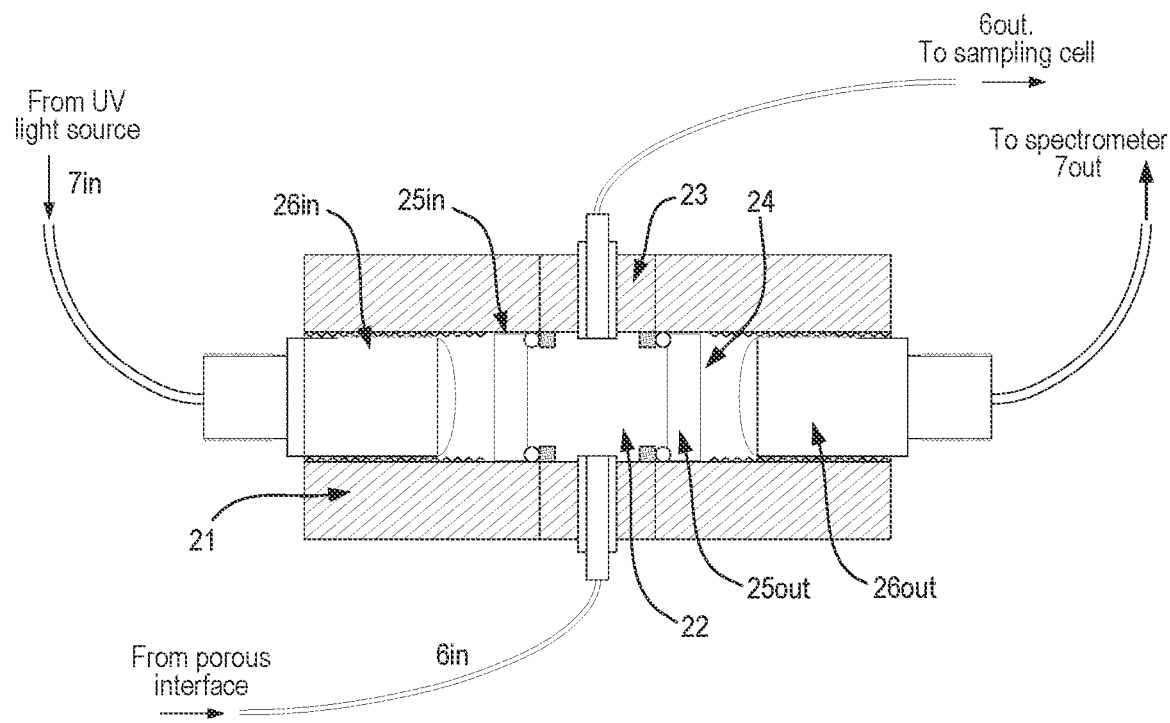
FIG. 5 illustrates a suitable design of the optical arrangement.

A suitable design of the optical arrangement, illustrating the path of the light beam is shown in FIG. 5. The optical flow cell (2) comprises a housing (21) with a small cavity (22)—the volume of the cavity is about 1-2 ml—formed by the intersection of two perpendicular aligned bores, one (23) for the flow of the porewater stream arriving from the porewater sampler (1) and the other (24) for transmittance of the beam generated by the light source (5) travelling through optical fiber (7) (Suitable fibers are commercially available, for example, StellarNet 'F600-UVVis-SR Armored Fiber Optics' optical fiber). Two transparent windows are oppositely positioned (25) to prevent the flow of the aqueous stream from cavity (22) into light transmitting bore (24), e.g., the windows are mounted in the optical flow cell but other arrangements where the windows are located at the end of optical probes inserted into the cell are also possible. In the specific cell configuration of FIG. 5, inner cavity is provided with two solar resistance quartz windows (25in, 25out) which allow the transmission of UV and deep UV ($\lambda<300$ nm) through collimating lenses (26in, 26out) such that the lenses are protected from a direct contact with the solution. Suitable collimating lens are commercially available, e.g., Stellarnet 'LENS-QCOL (UV grade)', and the connection to the optical fiber can be achieved with the aid of SMA-905 adapter.

Thus, light generated by light source (5) (e.g., UV lamp, for example, deuterium lamp), travels to optical flow cell (2) through optical fiber (7in) and is guided via collimator (26in) and transparent window (25in) into cavity (22). After passing through the solution located in cavity (22), the attenuated light exiting across transparent window (25out) is transmitted via the second collimator (26out) through an optical fiber (7out) to a spectrometer (8). More sophisticated optical designs are described below.

It should be noted that the light source and spectrometer may be external, where the light from the light source to the optical flow cell and from the optical flow cell to the spectrometer may be transmitted using optic fibers. The applied light source and the spectrometer are selected for the absorption range desired chemical constituent. Alternatively, whenever absorption wavelength of a specific chemical constituent is known, dedicated light sources and spectrometer of a narrow wave length ranges may be used simultaneously or separately.

It is seen that in the system illustrated in FIG. 3, an array of monitoring units is served by a single UV light source and a single detector. Hence the system needs to be configured to enable a single light source and spectrometer to make multi-point measurements. This can be achieved, for example, with the aid of an optical Fiber Multiplexer (OFM). In its most general form, OFM is a mechanical control unit which is used to divert the UV beam between a plurality of optical flow cells, allowing absorbance intensity measurement from multiple points/locations. The OFM uses a highly accurate step motor and a leading screw to move the optical fibers, UV lamp and spectrometer in order to place it in front of the chosen (stationary) optical flow cell. The OFM can be divided to a 'lower deck' consisting the UV lamp, spectrometer, step motor and instrument unit, and an 'upper deck' consisting an array of (stationary) optical flow cells.

Figure 16B:
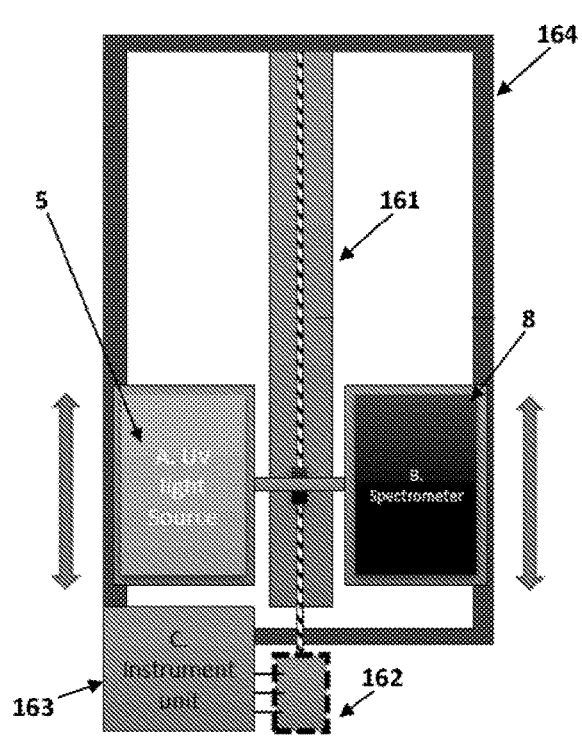
FIGS. 16A-16C illustrates one possible OMF.
Figure 16A:
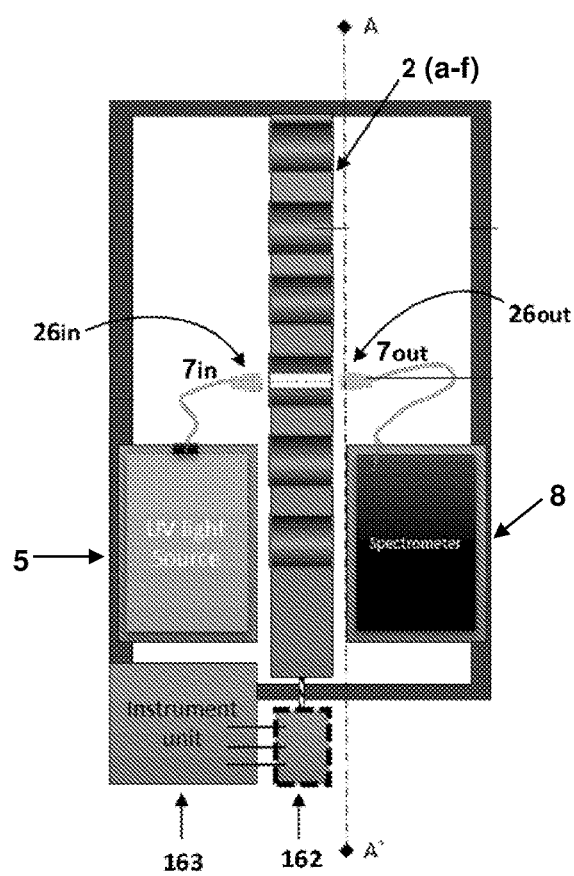
Figure 16C:
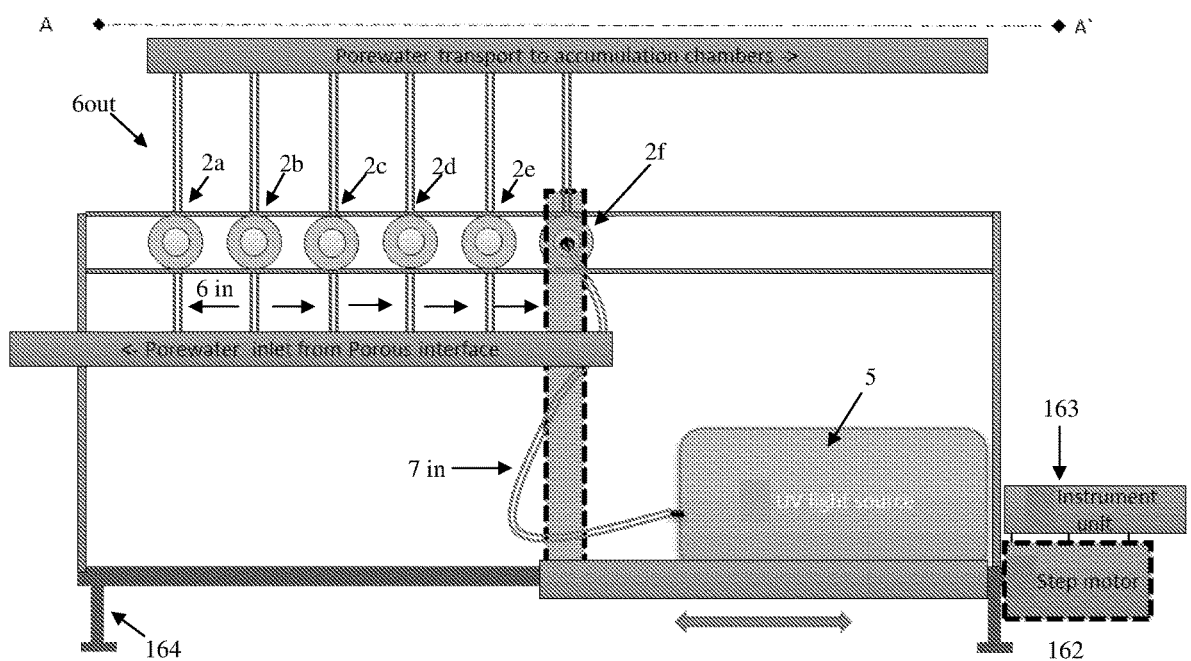

A top view of the 'upper deck' is presented in FIG. 16A, showing a set of spaced apart optical flow cells (2a), (2b), (2c), (2d), (2e) and (2f) mounted in a row with UV light source (5) and spectrometer (8) placed at the lower deck, on the opposite lateral sides of said row, such that when UV light source (5) and the spectrometer (8) are incrementally advanced along the lower desk, optical fiber (7in) terminated with a collimating lens (26in) and likewise optical fiber (7out) terminated with a collimating lens (26out) can be used to connect UV light source (5) and spectrometer (8) to the opposite sides of the light transmitting bore of each of the (2a), (2b), (2c), (2d), (2e) and (2f) optical flow cells sequentially. FIG. 16B provides a top view of the 'lower deck'. Leading screw (161), used to advance the UV light source (5) and spectrometer (8) couple, is driven by a step motor (162) controlled by instrument unit (163). FIG. 16C is the AA' cross section view of FIG. 16A, showing UV light source (5) moving along the 'lower deck' with optical flow cell (2f) being currently in operation, connected with optical fiber (7in) to UV light source (5). Also shown are the liquid flow paths, indicated by numerals (6in) and (6out)—the thin, preferably LDPE made, tubes directing incoming porewater stream from the porewater samplers to the respective optical flow cells (namely, tubes 6in), and outgoing porewater streams exiting the optical flow cells to their respective sampling cells (namely, tubes 6out). Frame (164) schematically indicates the structural support of the OMF.

The OMF shown in FIG. 16A-16C illustrates just one possible approach towards enabling the system of the invention to utilize a single light source (5) and spectrometer (8) while making multi-point serial measurements. Other approaches are based on movable optical flow cells relative to stationary single light source (5) and spectrometer (8) and/or movable mirrors for diverting the beam generated by the UV light source to and from each of the optical flow cells in turn.

Turning again to FIG. 3, it is seen that the porewater stream which exits the optical flow cell (2) flows through a small diameter tubing (6out, identical to the previously described 6in tube) to a sampling cell (3), which is capable of accommodating volume in the range from about 1 to 2 liter, for example.

Figure 6:
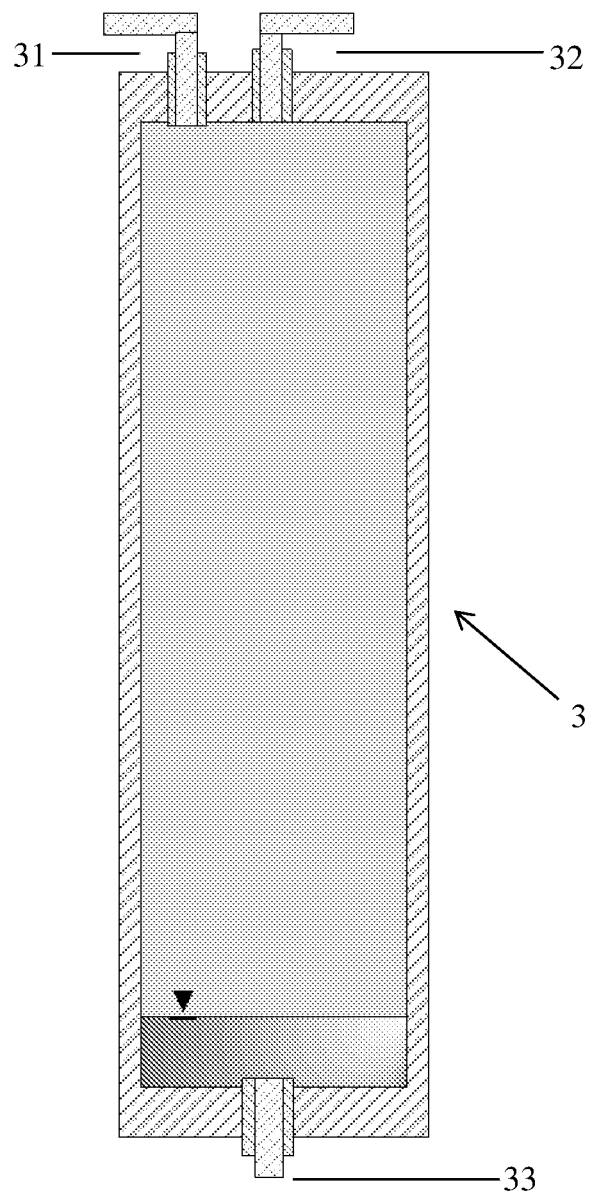
FIG. 6 illustrates a suitable design of the sampling cell.

A suitable design of a sampling cell (3) is shown in FIG. 6. Numerals (31) and (33) indicate the sample solution inlet connector and the sample outlet point, respectively. Numeral (32) indicates a vacuum charge point. The sampling cell (3) is charged with low pressure (vacuum) to enable the creation of tension that propagates from the sampling cell (3) through optical flow cell (2) down to the porewater sampler (1), causing soil porewater to flow from the porewater sampler (1) through the optical flow cell (2) to the sampling cell (3) where it is stored. The water sample accumulated in the sampling cell may either be analyzed occasionally upon request for the purpose of system calibration or quality assurance, as explained in more detail below, or drained back to the field. Once water from the sampling cell is sampled or drained, vacuum within the sampling cell (3) is restored using a mini vacuum pump that is operated automatically, and soil porewater flow through the optical flow cell (2) is resumed. The sampling cell body is made of polypropylene and can differ in volume and shapes, to suit for specific system designs and operational considerations. The chamber has inlet points to allow connection to the optical flow cell, sampling or drainage, and vacuum source, as indicated above. It may also contain a water level gauge for system control and sampling management.

As pointed out above, the determination of a suitable wavelength for detecting the analyte of interest (e.g., nitrate) and creation of a calibration curve poses a significant challenge to the accuracy of the measurement. Dissolved organic matter in water sources and particularly in soils contains a very wide range of complex organic molecules. Accordingly, the UV absorbance by the natural organic matter and interference with the nitrate absorption spectrum is controlled by the appearance of a large number of different organic molecules which vary from site to site and controlled by the bio-geo-climatic conditions. The present invention is based on a novel approach towards overcoming dissolved organic matter interference with nitrate absorption.

Briefly, a continuous scan of the absorption spectrum is used to set a "floating wavelength" which determines the optimal wavelength for calibration curve for nitrate concentration. Accordingly a site specific calibration curve is automatically generated by an algorithm that scans continuously the absorption spectrum. Experimental results reported below from field and laboratory experiments show that application of the "floating wave length" method enables real-time direct analysis of nitrate concentration in water samples obtained from a variety of soils where common UV absorption analysis failed to determine nitrate concentration due to interference of dissolved organic matter.

According to the present invention, a library (i.e., a collection) of calibration curves is associated with each individual sampling point in the field, or with a group of sampling points, or with the entire field (that is, all sampling points may share the same calibration curve). The calibration curves are generated by obtaining raw samples from one or more sampling points in the field, following which the raw samples are preferably spiked and diluted, to create a low and high concentration range solutions which are used to form calibration equations adoptable for the chemical composition of the porewater in each individual sampling point. During operation, a first calibration curve constructed at a first selected wavelength suitable for the current chemical composition of the soil and concentration range of said analyte is used; but when the concentration measured after some time is not within the original concentration range associated with the first calibration curve, then a second calibration curve pertaining to a different wavelength is chosen from the library and the system then switches to conduct further measurements with the aid of said second calibration curve, and so forth. The library is fairly stable;

such that measurements in each sampling point could lean on the 'local library' associated therewith for a long period of time, switching from one calibration curve to another within the library. However, it may happen that the library would have to be reconstructed, for example, following a significant agricultural or climatic event (e.g., addition of very large amounts of fertilizer to the field). In this case again the field would be sampled at the various sampling points, using porewater samples that accumulated in the sampling cells (3), to create a new collection of calibration curves.

A more detailed explanation is as follows:

1. Upon installation of all porewater samplers (component 1 in FIG. 3) in the monitored medium, a continuous stream of soil porewater begins to flow from each porewater sampler through the optical cell associated therewith (component 2 in FIG. 3) to the sampling cell (component 3 in FIG. 3) located downstream from the optical flow cell. The water samples are collected from the sampling cells and analyzed for concentration of target component through external analytical procedure.

2. During the initial sampling operation outlined above, a continuous scan of the absorption spectrum along the wavelength range is preformed to all porewater obtained from all cells. The selected range of wavelength is dependent on expected absorption of the target chemical constituent. For example, nitrate analysis through UV absorption should be scanned across the 190 to 850 nm range in each and every sample collected in stage 1.

3. The porewater samples, obtained in stage 1 and scanned by the monitored system in stage 2, are spiked and diluted to create a low and high concentration range solution which are used to form calibration equations adoptable for the chemical composition of the porewater in each individual sampling cell. All spiked and diluted samples are also scanned for their absorption spectrum at the entire wavelength range that was set in stage 2 (the optical flow cell is configured to enable calibration with external solutions, e.g., the aforementioned spiked or diluted solutions can be injected into the optical flow cell to obtain their spectrum).

4. The absorption spectrum of all original, spiked and diluted samples is analyzed to select the optimal wavelength (OWL) for concentration determination using a suitable wavelength selection procedure (see Example below).

5. The calibration equations that were determined for each monitoring unit by the optimal wavelength selection procedure, may contain a single OWL, as often found for a particular field, or may have multiple OWL for different concentration range. For example, high nitrate concentrations exceeding 100 mg/L may be determined in OWL of 300 nm, while lower concentration at the same monitoring unit at different time may be determine at 235 nm.

6. Since soil is a heterogeneous domain it is possible that the initial sampling in stage 1 and the absorption spectrum performed in stage 2 may yield a range of concentration that is wide enough to form a unique calibration equation on the basis of the natural concentration variation that has been measured in the field during stage 1. In that case it is possible that a unique calibration equation may generated without the need to follow the spiking and dilution process. Of course, such a calibration process (see Example 4) is limited to the range of natural concentrations found in the initial sampling.

7. As long as concentration measured by the method (as set by the absorption value in specified OWL) is within the range set in stage 3 or 4, than it is allowed to keep recording concentration values from each measurement point.

8. If concentration/absorption values measured exceed those obtained in stage 3 or 4, then switch to a different calibration curve (or return to stage 1 to reproduce calibration curves from the beginning as explained above).

Accordingly, another aspect of the invention is an adaptive wavelength hopping algorithm for choosing a wavelength for the spectral analysis and creation of a calibration curve, comprising the steps of:

A) obtaining a set of samples $S_i$ $\{S_1, S_2, S_3, \ldots, S_i, \ldots, S_n\}$ (for example, from the sampling cells);

B) determining concentrations $C_i$ ($C_1, C_2, C_3, \ldots, C_i, \ldots, C_n$) of said samples;

This can be achieved by either collecting n (or less) raw samples from n (or less) different locations in the field under study, or by collecting just one (or more) raw samples, and then spiking and/or diluting them; in any case the purpose is to have a reasonable concentration range of the analyte covered by $C_i$, to match with concentrations likely to be measured during future measurements in original porewater of specific chemical composition. The concentrations $C_i$ are determined using an external analytical procedure.

C) measuring the absorbance intensity versus wavelength across a predetermined range spanning the $\lambda_1$ to $\lambda_{final}$ region for each sample $S_i$ ($1 \leq i \leq n$), to ascribe to each sample $S_i$ a set of absorbance readings A(i) ($1 \leq i \leq n$):

$A(i)\{A(i)_{\lambda 1}, A(i)_{\lambda 2}, A(i)_{\lambda 3} \ldots A(i)_{\lambda k}, \ldots A(i)\lambda_{final}\}$, wherein $A(i)_{\lambda k}$ indicates the absorbance intensity measured for sample $S_i$ at a specific wavelength $\lambda_k$, for example, while it passes through the optical flow cell or using an external laboratory procedure.

For example, in the case of three samples flowing through the three optical flow cells arrangement shown in FIG. 3, the following is recorded, assuming that the 190-360 nm region is scanned:

$A(1)\{A(1)_{190\ nm}, A(1)_{\lambda 2}, A(1)_{\lambda 3} \ldots, A(1)_{\lambda k} \ldots, A(1)_{\lambda o}, \ldots, A(1)\lambda_{360\ nm}\}$ $A(2)\{A(2)_{190\ nm}, A(2)_{\lambda 2}, A(2)_{\lambda 3} \ldots, A(1)_{\lambda k} \ldots, A(2)_{\lambda o}, \ldots, A(2)\lambda_{360\ nm}\}$ $A(3)\{A(3)_{190\ nm}, A(3)_{\lambda 2}, A(3)_{\lambda 3} \ldots A(3)_{\lambda k}, \ldots, A(3)_{\lambda o}, \ldots, A(3)\lambda_{360\ nm}\}$ D) determining optimal wavelength $\lambda_o$ for calibration, by searching for a set of data consisting of $A(i)\lambda_o$ ($1 \leq i \leq n$) which fits the best to the set of data of known concentrations $C_i$ ($1 \leq i \leq n$);

For example, experimental work conducted in support of this invention indicates that satisfactory results can be obtained upon using a screening procedure placing two requirements on $\lambda_o$:

First, searching for all wavelengths $\lambda_k$ such that the strength of correlation between the known nitrate concentrations $C_i$ ($1 \leq i \leq n$) and absorbance intensities measured at said wavelength $A(i)\lambda_k$ ($1 \leq i \leq n$) is above a predetermined threshold, for example, using the R-squared test with R-squared value above a predetermined threshold, e.g. >0.9. Wavelengths showing R-squared below said threshold are rejected, with remaining wavelengths creating a set of candidate wavelengths.

Second, the set of candidate wavelengths is screened to locate $\lambda_o$, wherein $\lambda_o$ is characterized in that the slope of the straight line $C_i$ ($1 \leq i \leq n$) versus $A(i)\lambda_o$ ($1 \leq i \leq n$) is minimal. That is, exhibiting the highest variance $\sigma^2$.

Figure 17:
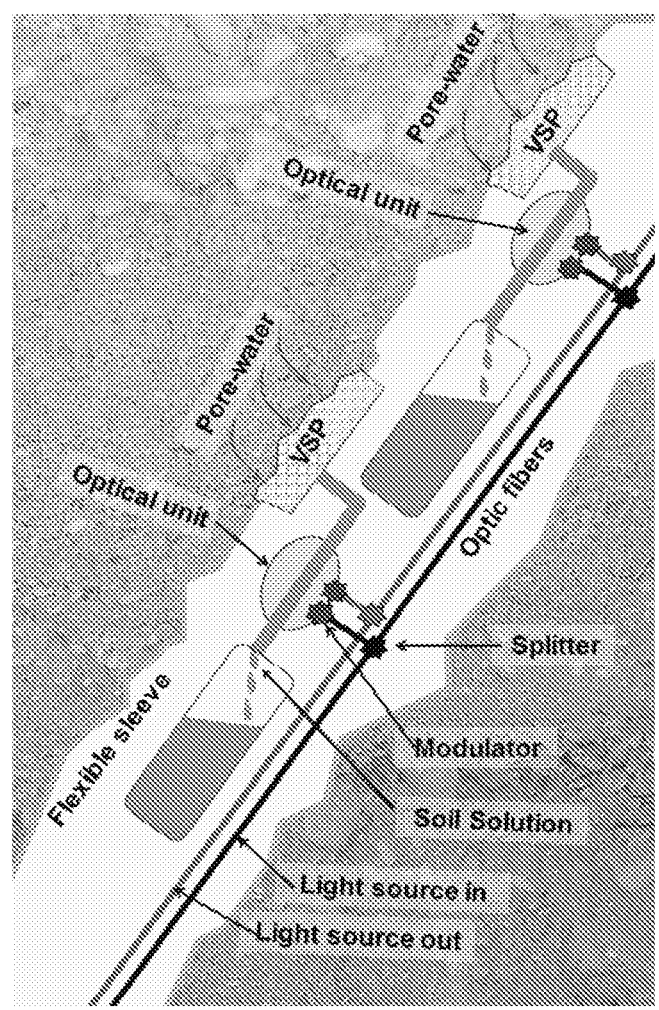
FIG. 17 shows that vertical deployment enables automated execution of nitrate (or other chemical species) concentration measurements across the entire unsaturated zone.

The description above illustrated the deployment of the system across a field, to create a network of sampling points in the field. But it should be noted that a 'vertical' deployment of the monitoring units is also possible, that is, positioning a plurality of monitoring units within a (sloped) borehole with the aid of vadose zone monitoring technology (VMS) based on an inflatable sleeve that is pressed against the walls of the borehole; as explained in detail in U.S. Pat. No. 8,381,582 and Turkeltaub, T., D. Kurtzman, and O. Dahan. 2016. Real-time monitoring of nitrate transport in the deep vadose zone under a crop field—implications for groundwater protection. Hydrol. Earth Syst. Sci. 20(8): 3099-3108. Such vertical deployment enables automated execution of nitrate (or other chemical species) concentration measurements across the entire unsaturated zone, as shown pictorially in FIG. 17; Pore-water solution driven continuously from the unsaturated sediment by the pore sampler analyzed continuously in the optical flow cell. This monitoring setup ensures automated continuous measurements, which saves the labor required in obtaining water samples from the field for lab analysis and enable remote real-time data acquiring.

Figure 18:
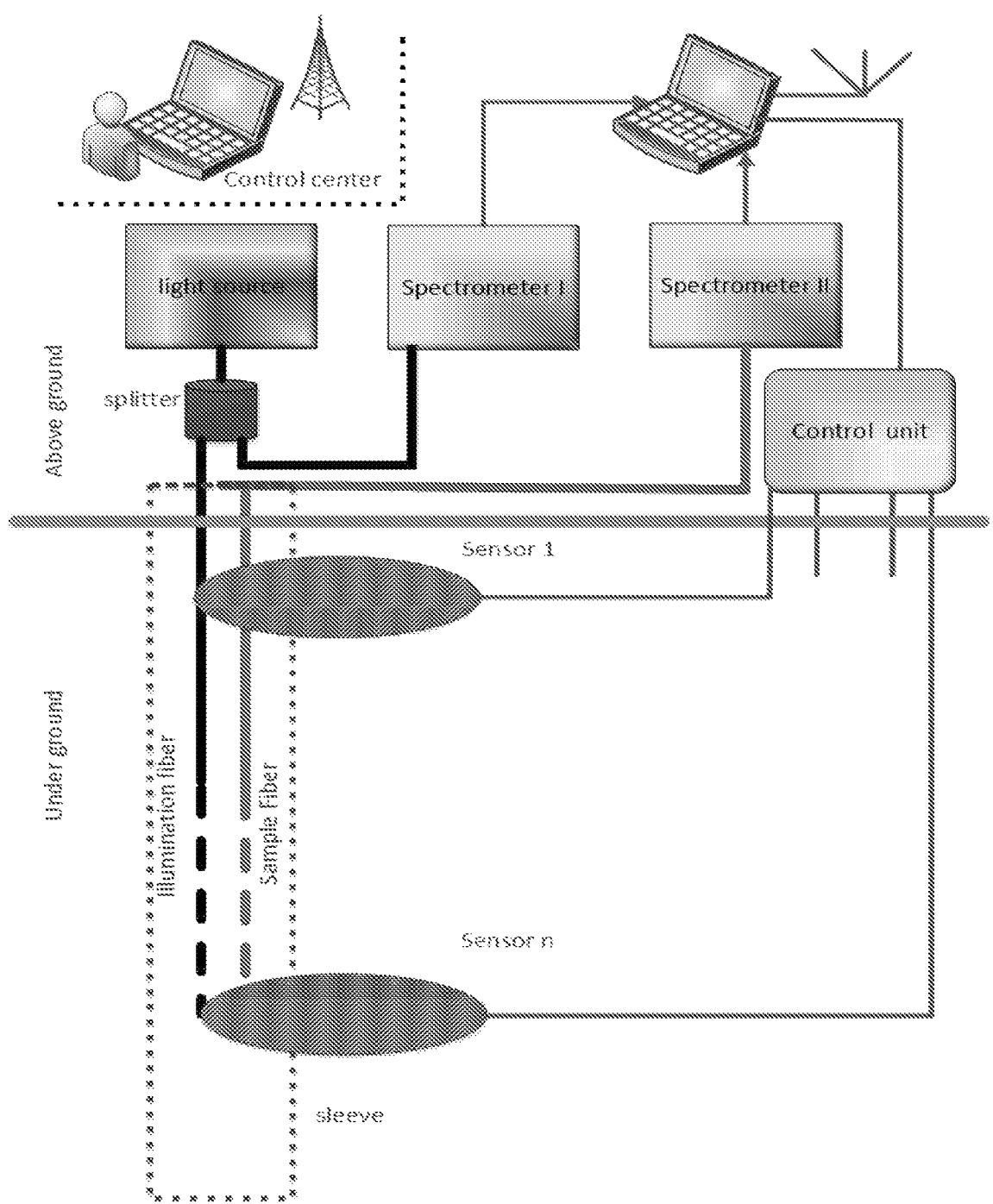
FIG. 18 shows that the vertically deployed system includes control centre and a plurality of nodes distributed in the area under monitoring.

Turning now to FIG. 18, it is seen that the proposed vertically deployed system includes control centre and a plurality of nodes distributed in the area under monitoring. The control centre receives information from the nodes in the fields by wireless communication (such as cellular, satellite, Wi-Fi or dedicate technology). Each node include deep well. A VMS sleeve with array of sensors is inserted into the well. The VMS sleeve is filled to achieve tight contact to the wall of the well. Then water samples can be analyzed in several locations along the well. The extract porewater is transferred through an optical flow cell through which the sample flows to a sampling cell. The sample holder, e.g., the optical flow cell is illuminated by optical light (e.g. UV to far IR). The light is created by light source that is attached to an optical fiber.

Figure 19:
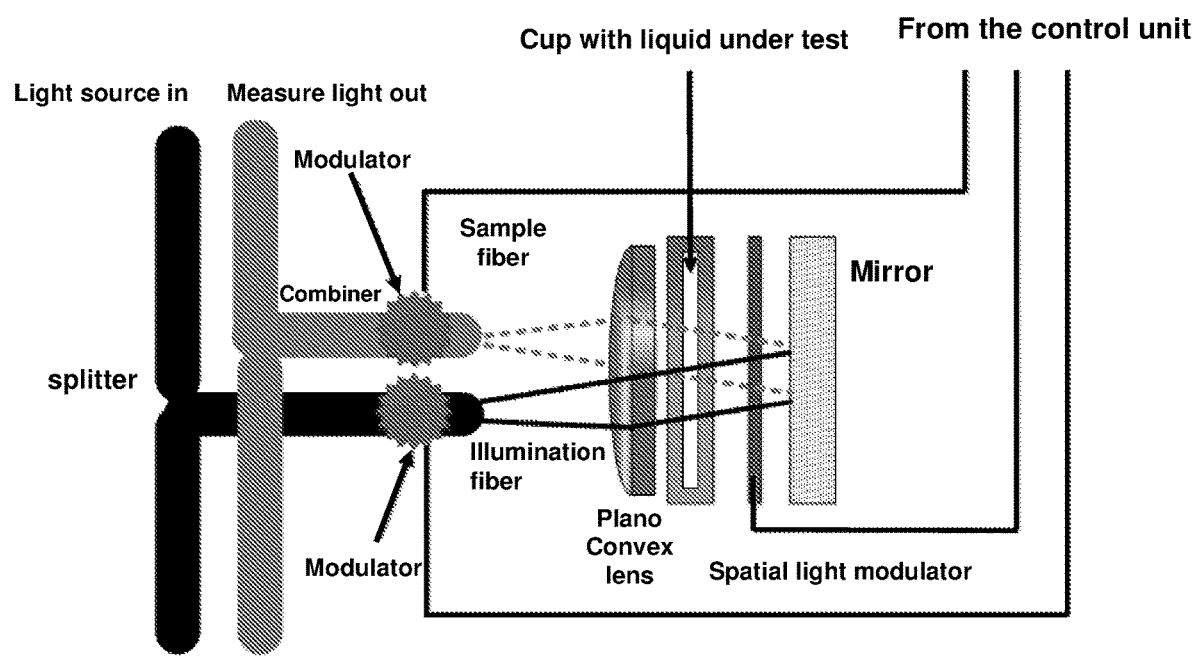
FIGS. 19-21 show several designs of sensors which can be incorporated into multi-point serial measurements based on a single light source and a single detector.
Figure 20:
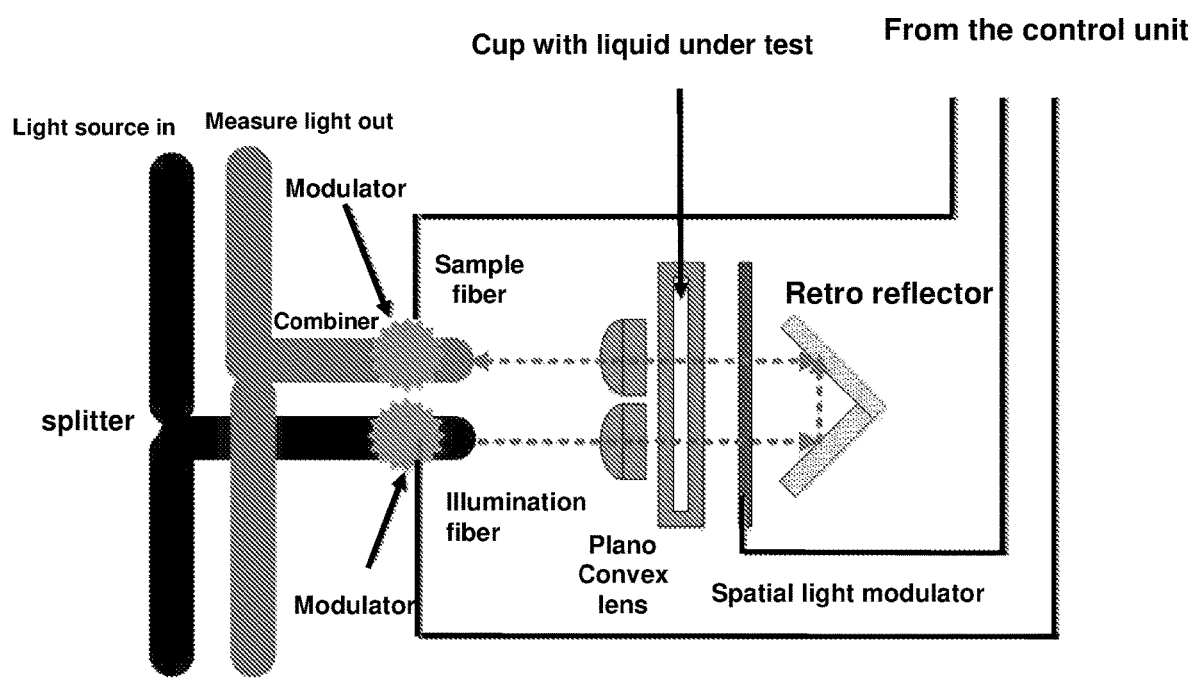
Figure 21:
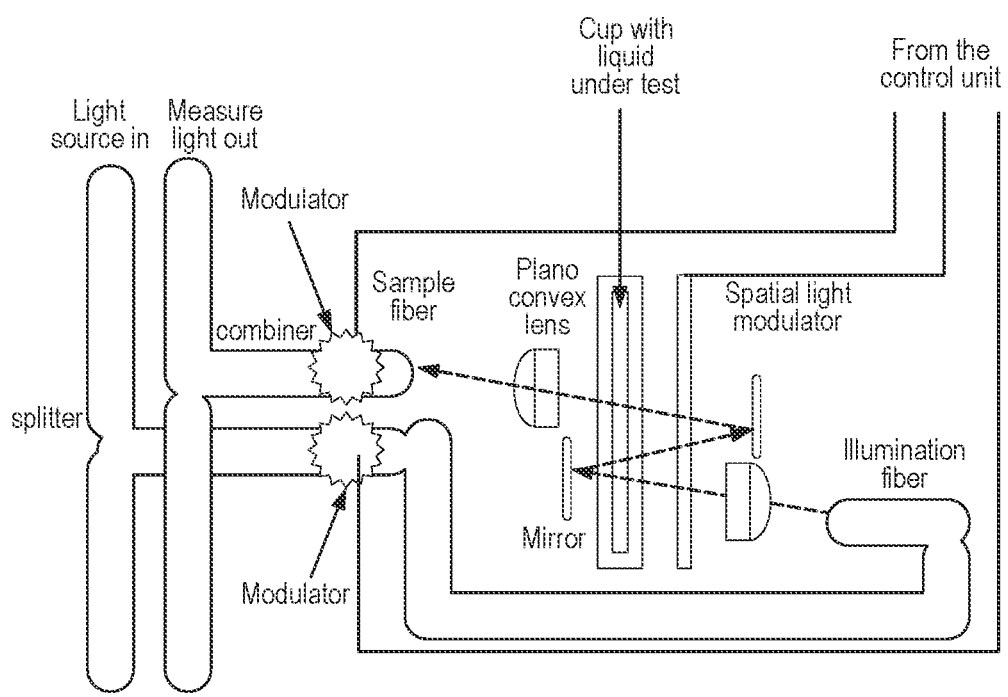

It is seen that the principles of operation of the 'horizontal' (namely, across a field) and 'vertical' (namely, VMS-based) deployments are essentially the same. It is of course possible to provide each of the vertically deployed monitoring units with its own light source and detector. However, a more cost effective approach would be to reduce the number of the light sources and detector, for example, to enable a single light source and spectrometer to make multi-point measurements. FIGS. 19 to 21 show several useful designs of sensors which can be incorporated into such multi-point serial measurements based on a single light source and a single detector.

As shown in FIGS. 19-21, the output of the fiber is focused on the sample holder by plano convex lens. Some of the light is absorbed by the water in the sample holder, the rest is propagate and reflect back by a mirror. The reflected light propagates again through the cup, partially absorbed whereas the rest is focused to the input of the sampling fiber. The output of the sampling fiber is connected to spectrometer, which measures the spectra of the received light. At the same time another spectrometer samples the light source in order to scale and calibrate the received sample. The output from the two spectrometers is transferred to the computer to local processing. At the end of the process the information is transmitted to the control center. However in order to sample more than one sensor at the same time, modulation of the signal from each sensor should be done at different frequency. The modulation could be achieved using one or more of the following options: modulator at the output of the illumination fiber, at the input of the sampling fiber, or by placing spatial light modulation before the mirror. The control of the modulator is done by the control unit connected to a computer. The computer dictates different modulation frequency to each of the sensor at one or more modulation options. In the case of array of sensors the output from the spectrometer is analysed by signal processing methods so the signal from each sensor could be identified. The contamination in the water is then calculated according to known algorithms.

Accordingly, another aspect of the invention is the system as described above, wherein the optical flow cell has a front face through which a light beam travelling from the light source via an illumination optical fiber enters said optical flow cell, and a rear face through which a light beam exiting the optical flow cell is guided via a sample optical fiber to the detector, wherein the optical flow cell is provided with an optical arrangement comprising at least one of the following:

one or more lenses (e.g., plano convex) mounted in the front and/or rear side of said optical flow cell;

one or more deflectors and/or mirrors mounted in the front and/or rear side of said optical flow cell;

wherein the optical arrangement is configured to focus the light beam traveling via the illumination optical fiber onto said optical flow cell; to reflect light beam exiting said optical flow cell back to said optical flow cell; such that the front and rear side are interchangeable;

and wherein the system further optionally comprises one or more of spatial light modulator and/or modulators at the output of said illumination fiber or inlet of said sample fiber wherein each optical flow cell is associated with a specific code or frequency, the system further comprising a control unit and a computer to assign each monitoring unit with said code or frequency.

It may be appreciated that various systems configured to enable a single light source and spectrometer to make multi-point measurements of a liquid sample by light spectrometry, can benefit from the optical geometry described above. Hence another aspect of the invention is a device for detecting an analyte in a plurality of liquid samples with the aid of light spectrometry, wherein the device comprises at least one light source, a plurality of sample holders (e.g., an optical flow cell or a cuvette), and at least one detector, wherein each sample holder has a front face through which a light beam travelling from the light source via a wave guide (e.g., illumination optical fiber) enters said optical flow cell, and a rear face through which a light beam exiting the optical flow cell is guided (e.g., via a sample optical fiber) to the detector, wherein the sample holder is provided with an optical arrangement comprising at least one of the following:

one or more lenses (e.g., plano convex) mounted in the front and/or rear side of said sample holder;

one or more deflectors and/or mirrors mounted in the front and/or rear side of said sample holder;

wherein the optical arrangement is configured to focus the light beam traveling from the light source onto said sample holder; to reflect light beam exiting said sample holder back to said sample holder; such that the front and rear side are interchangeable;

and wherein the device further comprises one or more of spatial light modulator and/or modulators (e.g., at the output of an illumination fiber or inlet of said sample fiber) wherein each sample holder is associated with a specific code or frequency, the device further comprising a control unit connected to a computer to assign each sample holder with said code or frequency.

EXAMPLES

Example 1

Figure 1A:
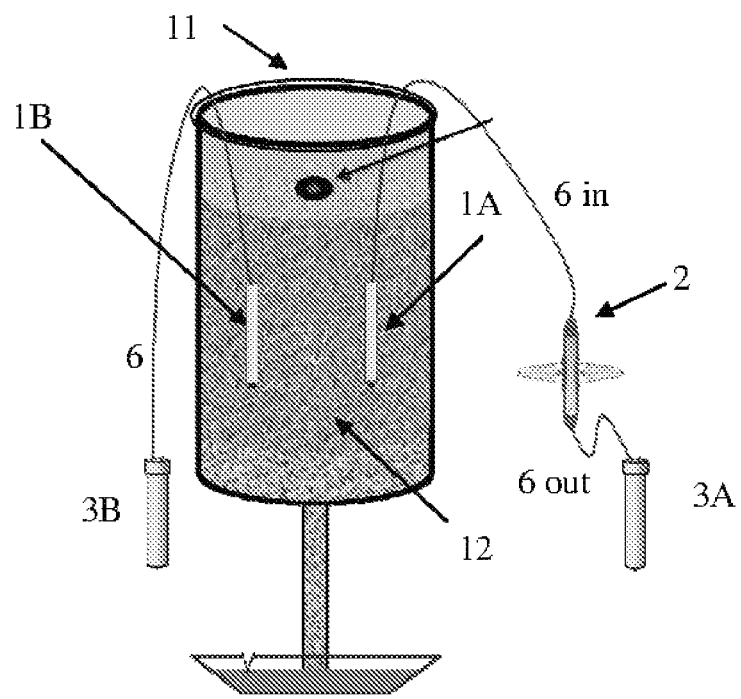
FIGS. 1A-1B show an experimental setup; showing the sample flow and optical arrangements; respectively.
Figure 1B:
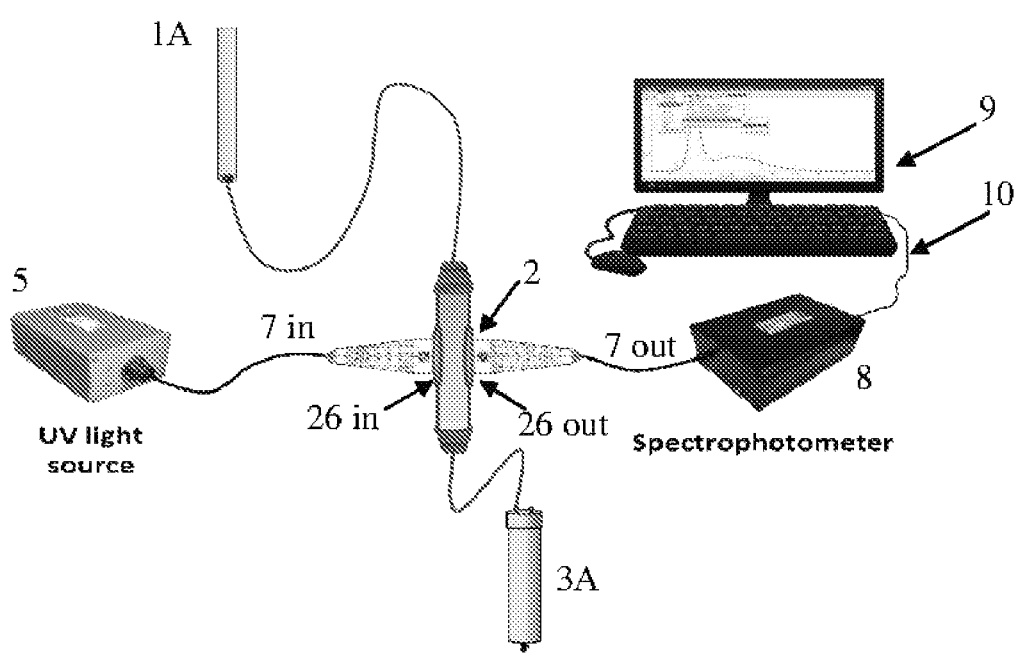

Measurement of Nitrate in a Solution Extracted Continuously from Soil with the Aid of UV Light Spectroscopy The experimental setup is illustrated in FIGS. 1A and 1B, showing the sample flow and optical arrangements, respectively.

Starting with FIG. 1A, a column indicated by numeral 11 was filled with 25 kg of sandy soil 12. The column used is a 5 gallon flowerpot. A porewater sampler 1A consisting of a cylindrically shaped vessel with a porous interface as described above in reference to FIG. 4 is installed in the sand, such that its lowermost end is about 20 cm below the level of the soil in the column. Porewater sampler 1A is connected with a 300 cm long capillary tube 6in having an inner diameter of 1.6 mm to the fluid inlet port of an optical flow cell 2 (with the design described above in reference to FIG. 5). A sampling cell 3A is placed downstream to the optical flow cell 2, such that outgoing liquid stream exiting optical flow cell 2 is discharged to, and collected in, vessel 3A. It is seen that in addition, a porewater sampler 1B identical in shape, size and structure to 1A is also installed in the sand. Porewater sampler 1B discharges directly to a sample accumulation vessel 3B through a thin tube 6. That is, there is no optical flow cell placed along the path connecting the outlet port of porewater sampler 1B and the inlet of sample accumulation vessel 3B such that the pair 1B-3B serves for control measurement as explained below. A dripper was used for application of water.

Turning now to FIG. 1B, it is seen that the optical arrangement consists of a UV light source 5, e.g., a deuterium lamp (SL3 Deuterium Light Source for UV, equipped with 'DCX' Lens for higher intensity performers, manufactured by StellarNet Inc; the lamp emits UV light over the 190-450 nm range). The light travels from the lamp via an optical fiber 7in ('F400-UVVis-SR' Armored, 2 meters, solarization resistant fiber optic cable available from StellarNet Inc), through the optical flow cell 2 and to spectrometer 8 ('BLACK-COMET UV-VIS' Spectrometer from StellarNet Inc, designed to measure transmissivity and absorbance between 190-850 nm; the spectrometer is connected to a computer 9 via USB cable 10 and controlled by 'SpectroWiz', StellarNet provided software). As shown in FIG. 1B, sets of collimating lenses 26in and 26out (5 mm diameter, UV-Vis, purchased from StellarNet Inc) are placed on opposite sides of the transparent surface of the optical flow cell body 5. That is, to better collect and transmit the scattering ray as it exits and enters the optical fiber (7in-7out). The lenses were terminated by a SMA-905 optical fiber connector, which enabled connection between the optical flow cell, the spectrometer and the UV light source.

Returning back to FIG. 1A, the experiment started by injecting a single nitrate pulse of 1000 mg $L^{-1}$ at the top of the column (1) and the propagating plum of nitrate has been monitored throughout the experiment as the column had been irrigated on daily cycles (1 L of tap water, hence nitrate concentration added was well below 50 mg $L^{-1}$). The experiment lasted ten days, and during this time period three sets of data were recorded:

1) using the optical online monitoring setup to periodically measure UV absorbance of the nitrate solution passing through optical flow cell 2 at intervals of two hours. Nitrate concentration (ppm) was calculated according to 235 nm absorbance intensity.

2) sampling water from sampling cell 3A (one to three times per day) and determining nitrate concentration with the aid of DIONEX ICS 5000 ion chromatograph.

3) sampling water from accumulation vessel 3B (one to three times per day) and determining nitrate concentration with the aid of DIONEX ICS 5000 ion chromatograph.

Figure 2:
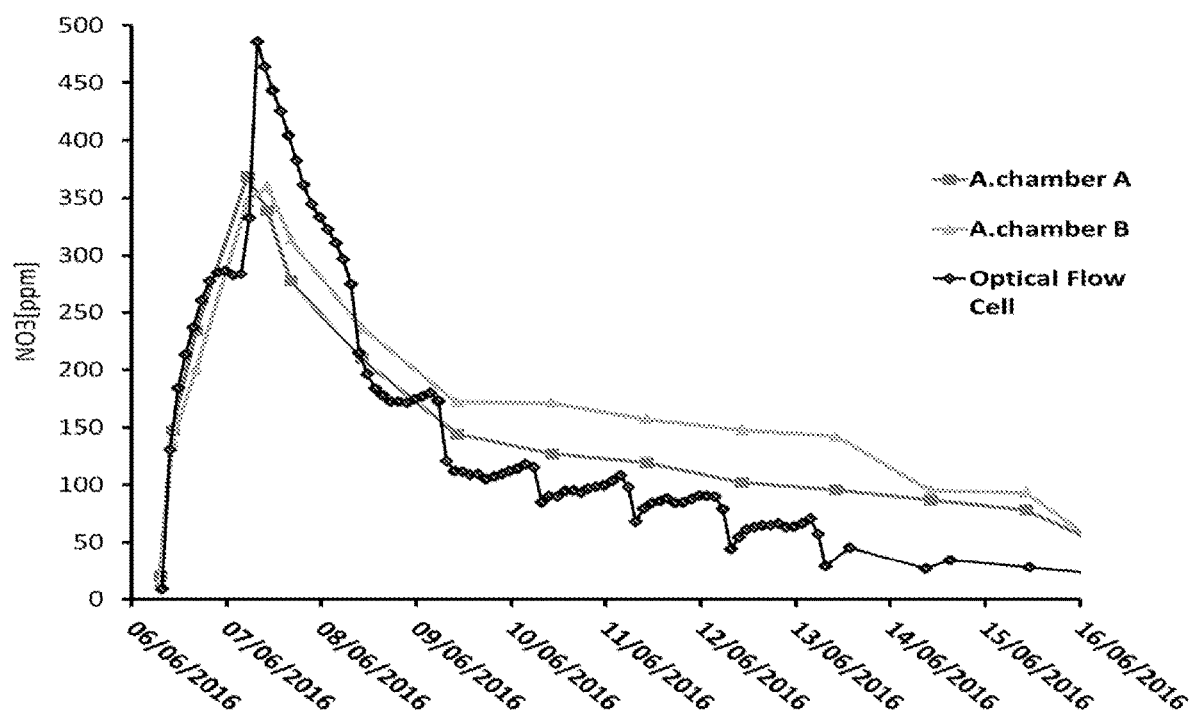
FIG. 2 presents nitrate concentration (ppm) versus time curves generated on the basis of different sets of data.

The results are shown in FIG. 2, which presents nitrate concentration (ppm) versus time curves generated on the basis of each set of data ((1) is marked with black rhombuses, (2) by green triangles and (3) by red rectangles). It is seen that the curves are fairly consistent, showing almost identical trends. As an aside, it is noted that the results obtained by the optical flow cell indicate slightly higher concentrations of nitrate at the beginning of the breakthrough curve compared to the other methods; this can be explained by the differences in the way the sample is being collected and the data is being generated. Online monitoring in the optical flow cell 2 (that is, method 1) enables the measuring of nitrate concentration in the solution just as it being extracted from the soil pores, whereas the plots generated on the basis of samples taken from the accumulation chambers 3A and 3B (methods 2 and 3) indicate the average of the soil solution nitrate concentration between sampling events, thus physical sampling of soil solution would underestimate the nitrate concentration in the soil pores and hence the slightly lower concentrations shown by the curves assigned to the measurements by methods 2 and 3. Additionally, the high-resolution monitoring in time had revealed the rapid changes in nitrate concentration which occur in soil during water percolation events.

Example 2

Measurement of Nitrate in a Solution Extracted Continuously from Soil with the Aid of UV Spectroscopy The experiments reported in this study are based on the soil-packed column set-up described in Example 1. But this time three large-scale columns were used, to test three different types of soils, with two monitoring units coupled to each column. An individual monitoring unit consists of a porewater sampler (1), an optical flow cell (2) and a sampling cell (3) as described in the previous example. A single optical arrangement as previously outlined is also implemented for continuous and simultaneous measurement in six units placed in the three soil columns.

Three soil-packed columns were used:

Column 1 was filled with about 170 kg of fine sand soil; the top layer was mixed with compost 10% by weight.

Column 2 was filled with about 170 kg of fine sand soil.

Column 3 was filled with about 185 kg of clay soil.

Figure 7A:
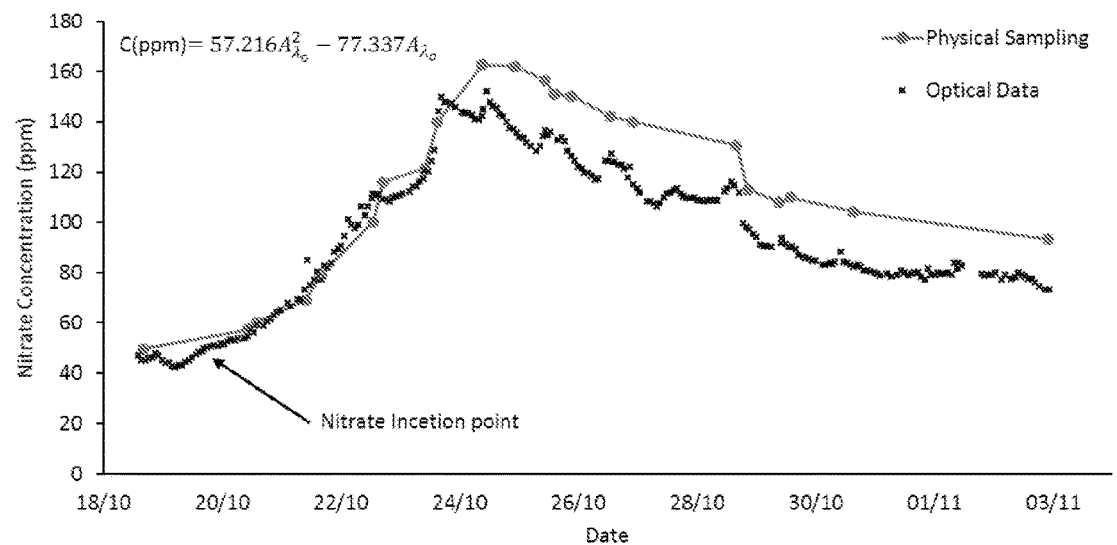
FIGS. 7A-7F are experimental results shown as nitrate plots versus time.
Figure 7B:
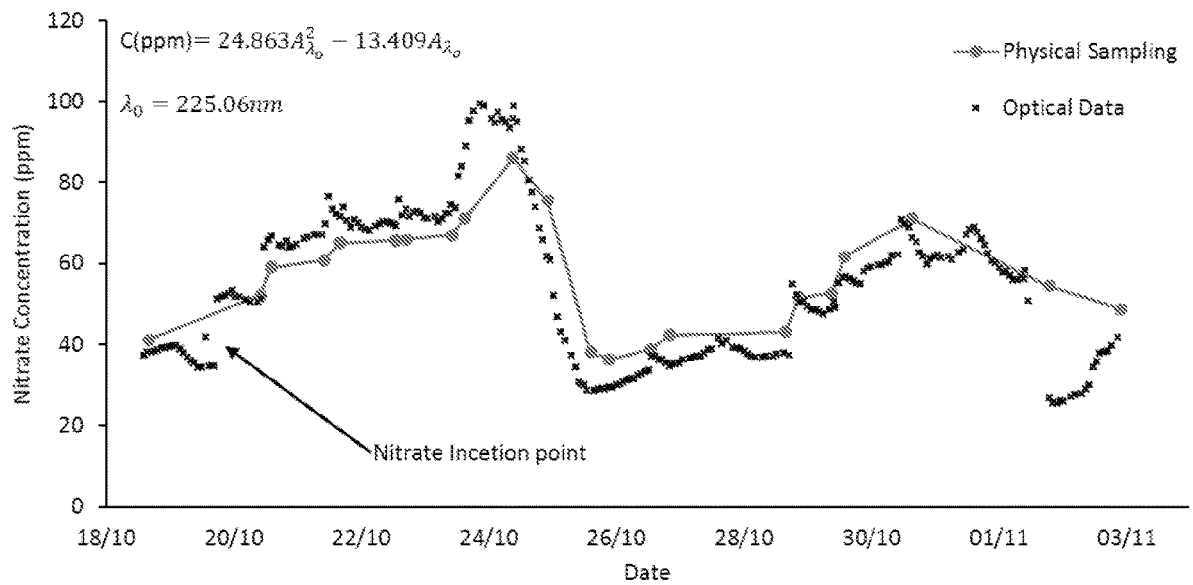
Figure 7C:
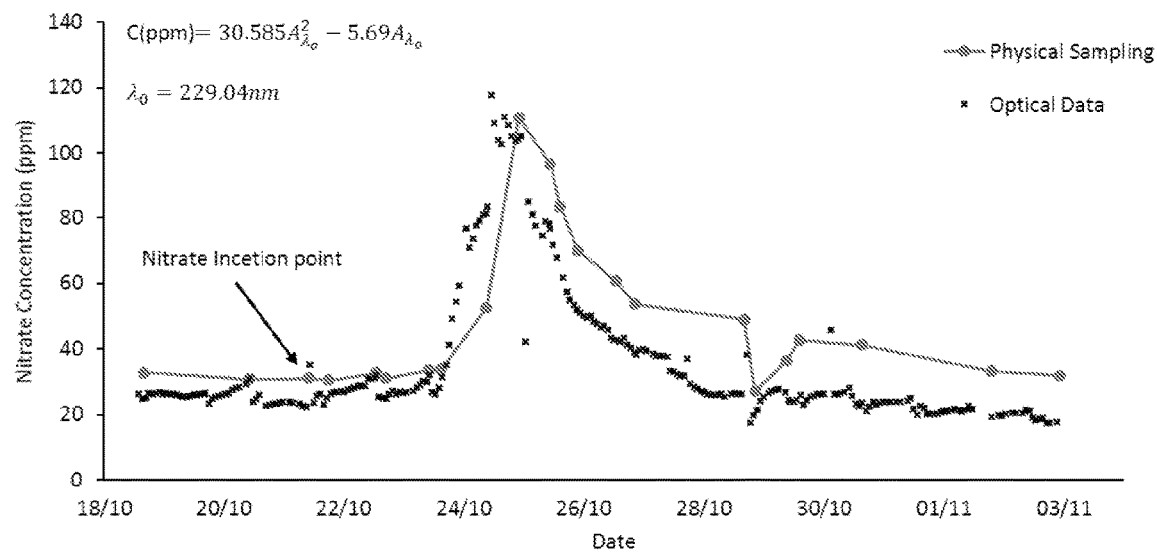
Figure 7D:
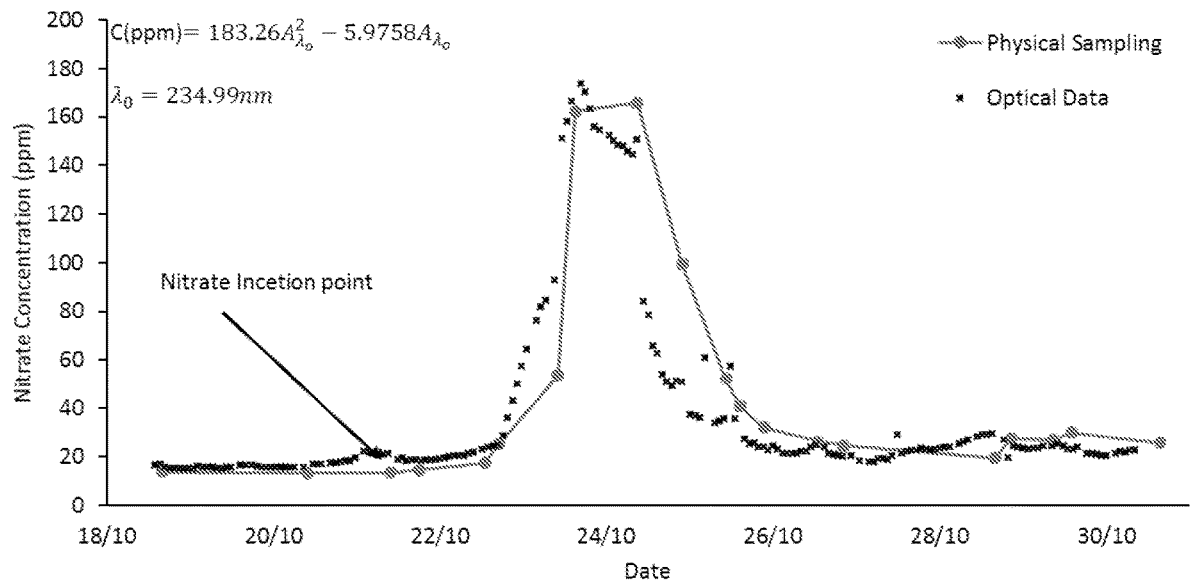
Figure 7E:
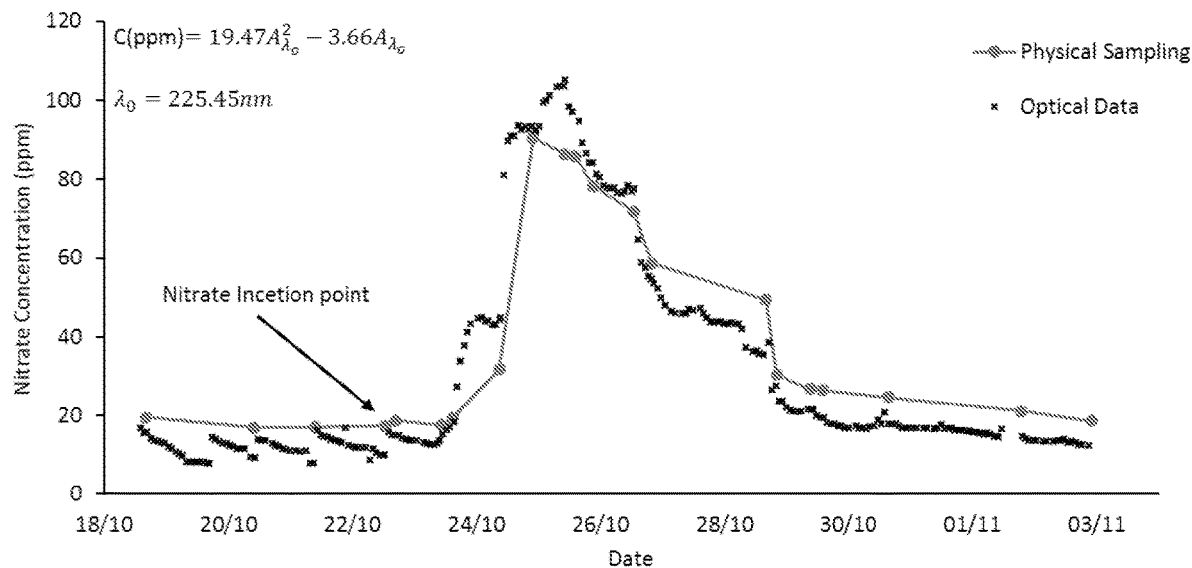
Figure 7F:
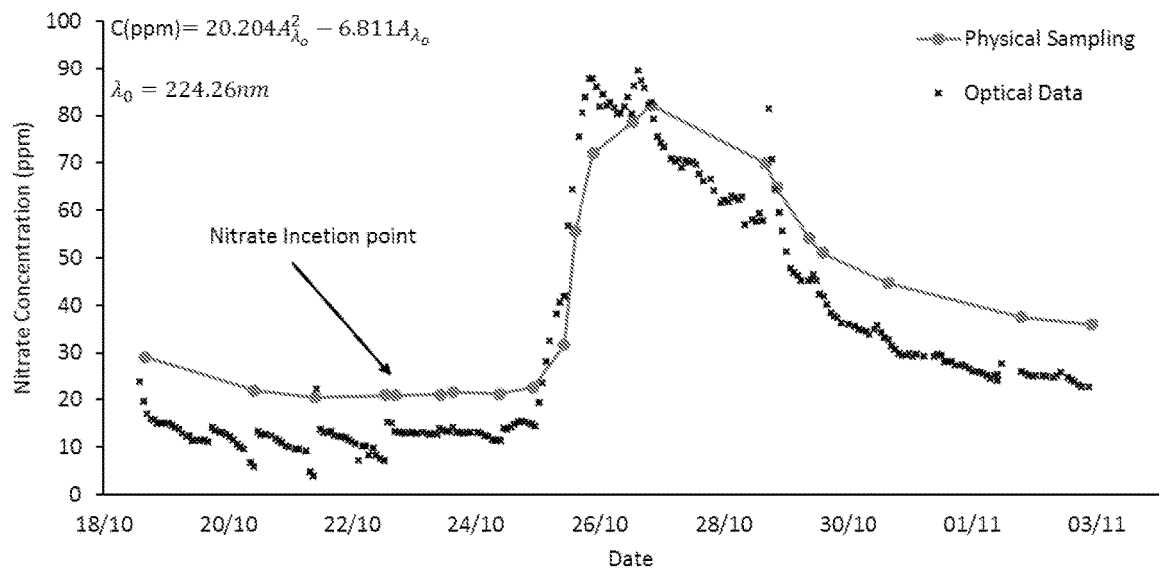

The results are shown in FIGS. 7A-7B as nitrate concentration plots versus time (7A and 7B for column 1, 7C and 7D for column 2 and 7E and 7F for column 3). Absorbance intensities were taken at intervals of two hours over a period of about two weeks to determine variation in nitrate concentration with the passage of time with the aid of UV spectroscopy in the optical flow cell (curves marked by black squares in each of the 7A-7F graphs). Physical sampling directly from sampling cell located downstream to the optical cell in each monitoring unit was carried out once or twice a day, and nitrate concentrations in the periodically collected samples was measured using Deionix Ions analyzer. The time at which nitrate solution (1000 mg L$^{-1}$) was injected at the beginning of the each experiment is also indicated in the graph. The columns were occasionally irrigated during the experiment, three times a day with 1 L irrigation at each irrigation event.

Nitrate concentration plots versus time obtained with the aid of UV spectroscopy in an optical flow cell, in which the extracted water was allowed to flow continuously, are fairly consistent with the curves generated on the basis of data obtained from the samples by different methods (either DIONEX ICS 5000 ion chromatograph or TOC, DOC, TN, DN multi N/C 2100s 'AnalytikJena' analyzer, which gives equivalent of nitrate concentration by multiplying the total nitrogen value by 4.43).

Example 3

Applicability of Nitrate UV Spectral Analysis in Soil Pore-Water Samples

To test the applicability of nitrate spectral analyses of soil solution samples, two approach are demonstrated, one based on a general calibration curve and the other on creation of an individual calibration curve associated with each field.

Part A: Creating a General Calibration Curve

Water samples were collected from VMS that was installed at four different study sites: (1) an open field, (2) an orchard, (3) a conservative greenhouse and (4) an organic greenhouse. Nitrate concentration was determined using 'DIONEX ICS 5000', Ion chromatograph. Table 1 tabulates the nitrate concentrations measured for several samples collected at different ports of the VMS, for each of the four sites under study:

TABLE 1

| | $NO_3^-$ [mg/L] | | | |
| --- | --- | --- | --- | --- |
| VMS port | Organic greenhouse | Conservative greenhouse | Orchard | Open field |
| 1 | 182 | 412.4 | N/A | N/A |
| 2 | 251 | 337.6 | 45.2 | N/A |
| 3 | 366.75 | 579.75 | 54 | 1636.5 |
| 4 | 598 | 506.8 | 58.5 | 1014.5 |
| 5 | 431.25 | N/A | 74.6 | 505.5 |
| 6 | 357.75 | 83.8 | 59 | 310 |
| 7 | 298.44 | 158.2 | 75.5 | 226.2 |

Additionally, the total concentration of nitrogen and organic carbon in the samples was determined using TOC, DOC, TN, DN multi N/C 2100s 'AnalytikJena' analyzer.

The results tabulated in Table 1 indicate that nitrate concentration in the solution typically ranges between few hundreds and few thousands mg L$^{-1}$. Accordingly, the 301 nm wavelength was chosen for UV measurements in order to establish a correlation between the results tabulated in Table 1, which are based on ion chromatography, and UV absorbance intensity values, to create a calibration curve.

Figure 8:
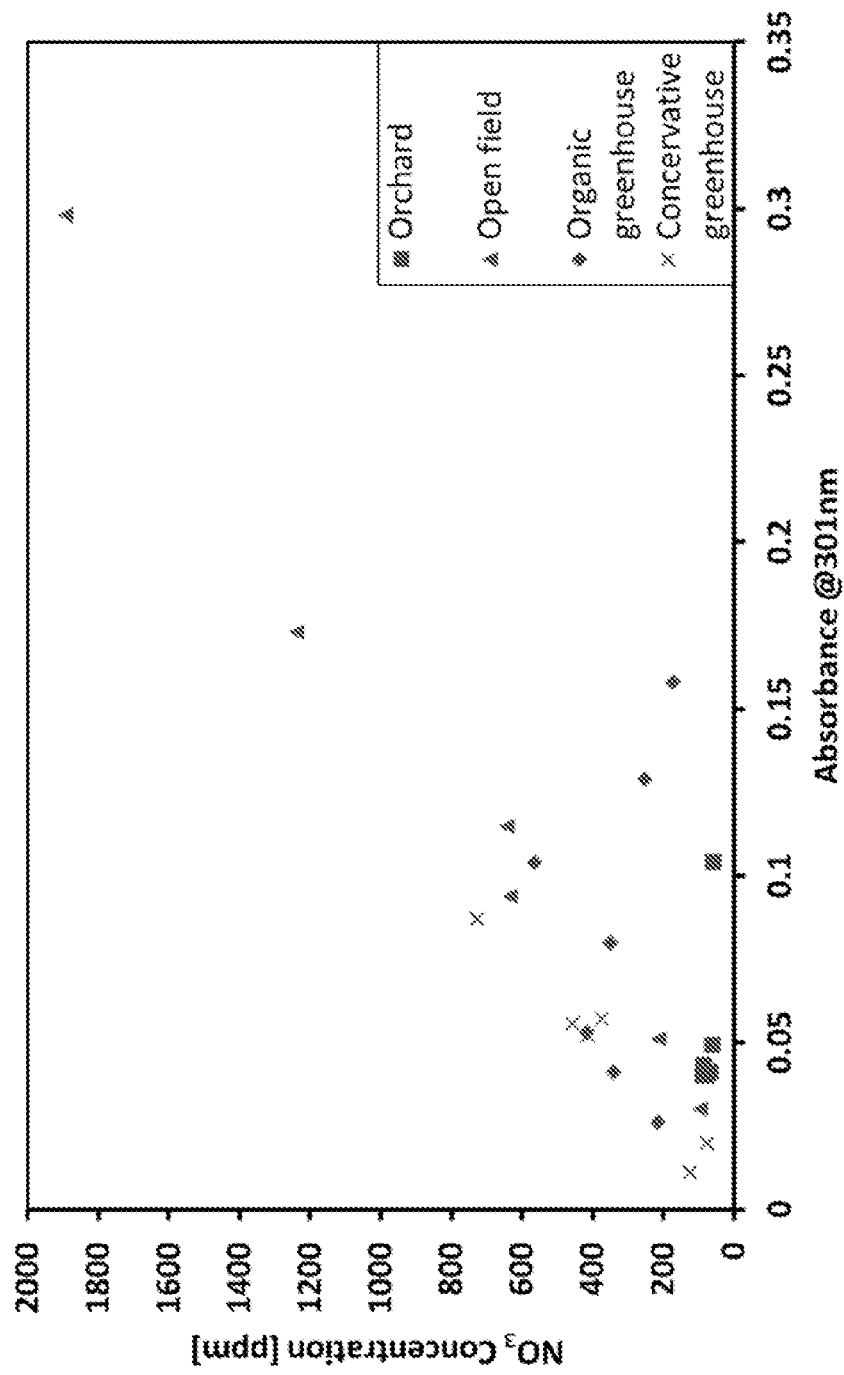
FIG. 8 shows nitrate concentrations measured by DIONEX ICS 5000 ion chromatograph are plotted against 301nm absorbance intensity values, obtained by a desktop spectrometer.

But attempts to establish a calibration curve leaning of the 301 nm peak absorbance intensity met with difficulties. In FIG. 8, nitrate concentrations measured by DIONEX ICS 5000 ion chromatograph are plotted against 301 nm absorbance intensity values, obtained by a desktop spectrometer. Very low to no correlation has been found between the two sets of values, and a general calibration curve could not have been produced.

Figure 9:
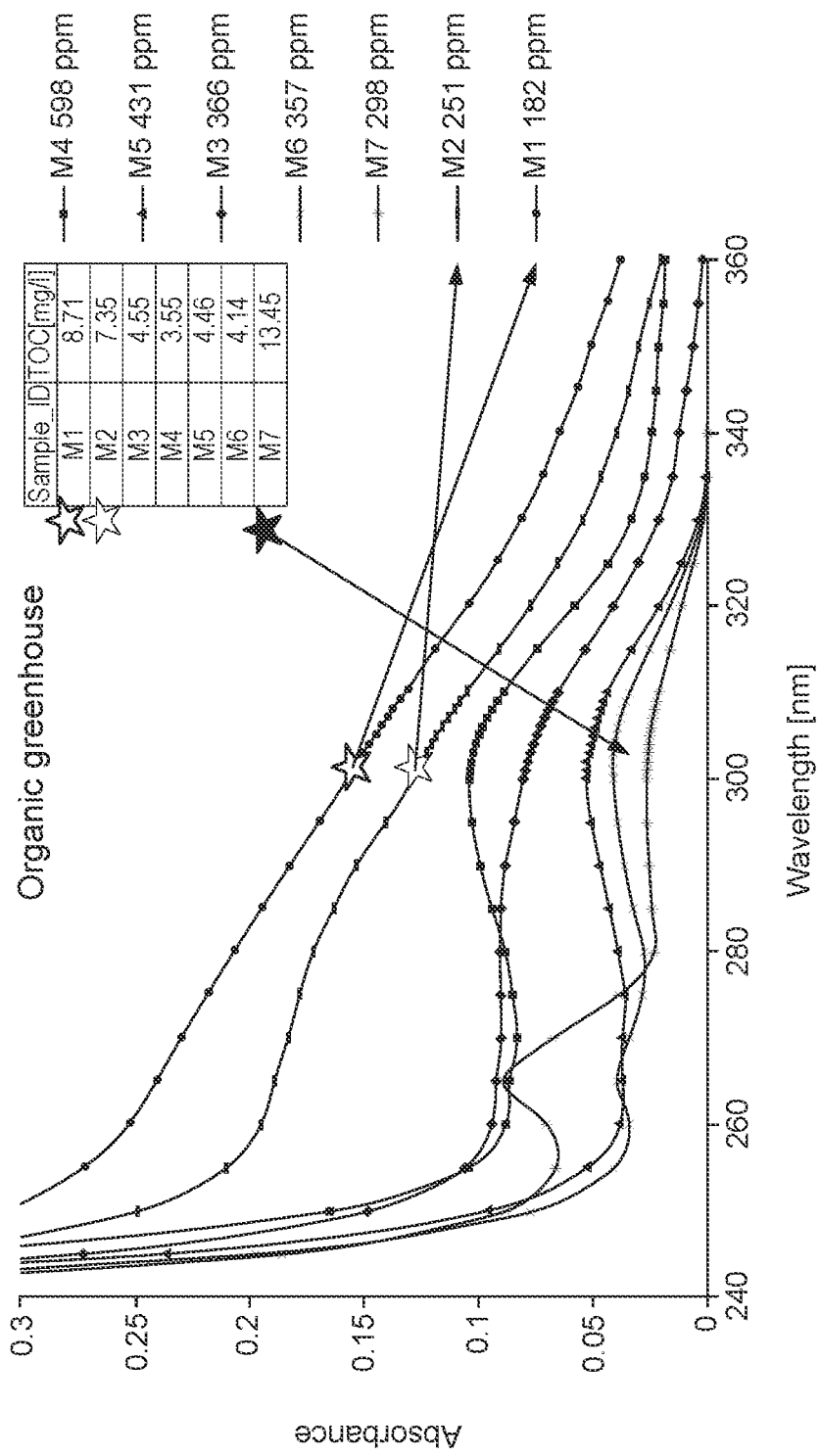
FIG. 9 shows UV spectra recorded for the seven samples collected in the organic greenhouse.

For example, UV spectra recorded for the seven samples collected in the organic greenhouse are presented in FIG. 9 (the samples are designated M1-M7 in line with the data in the corresponding column in Table 1 above). It was noted that samples "M1" and "M2" had the highest absorbance intensity, yet the lowest nitrate concentration determined by ion chromatography, suggesting the possibility of a masking effect caused by the presence of DOC. However, at the same batch of results, sample "M7" has the highest concentration of DOC yet the lowest absorbance intensity. Thus, the possibility of masking by DOC seems to be unlikely.

Lack of consistency between absorbance intensities to nitrate concentrations in the field samples strongly suggests that DOC in soil solution is a "soup" containing hundreds of different organic molecules. As such, DOC chemical composition is not homogenous and is varying between the different field sites. Therefore, the nature of the interference and the impact it creates on the nitrate analyses would be different depending on the DOC chemical composition at each of the different study sites. The conclusion drawn from the results reported above is that there cannot be one correlation line, or a calibration equation, that would be suitable for all different fields, or even for the different sampling points in the same field.

It was therefore decided to try a different approach, namely, assign each of the different field stations with a unique calibration equation. This approach is demonstrated below.

Part B: Creating an Individual Calibration Curve

Figure 10:
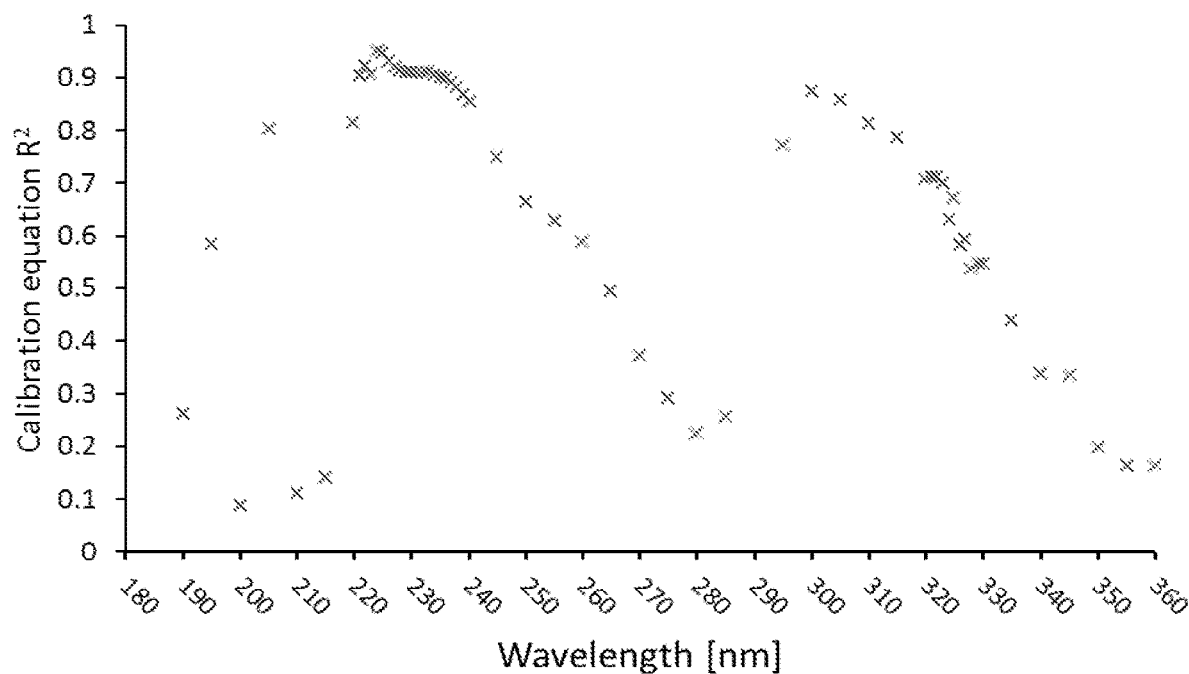
FIG. 10 demonstrates the calibrating scheme for the orchard field station.

Stitching an individual calibration equation had been done by scanning the absorbance spectrum to find at which wavelength the absorbance intensities vectors correlate best with the measured nitrate concentration vectors. FIG. 10 demonstrates the calibrating scheme for the orchard field station. It can be perceived from the graph that the best correlation would be achieved at 225 nm wavelength, between absorbance intensities and solution nitrate concentrations (the ordinate in FIG. 10 is the calculated R-squared parameter at each wavelength—see next example illustrating a procedure for choosing a suitable wavelength for UV spectroscopy analysis of nitrate in porewater).

Figure 11:
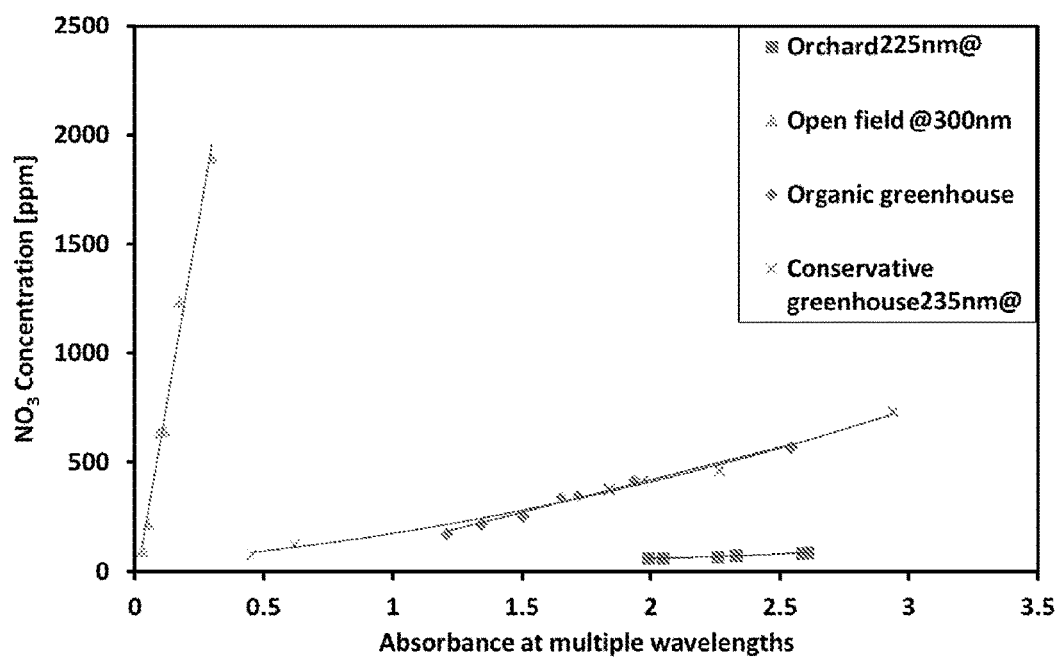
FIG. 11 shows nitrate concentration obtained by DIONEX ICS 5000 ion chromatograph against absorbance intensity at multiple wavelengths.

The new method was applied on all field samples and an individual calibration equation has been generated to each of the study sites. FIG. 11 shows nitrate concentration obtained by DIONEX ICS 5000 ion chromatograph against absorbance intensity at multiple wavelengths. It is seen that each of the field stations has been successfully assigned with an individual own calibration curve, generated by the most suitable wavelength for each field.

Figure 12:
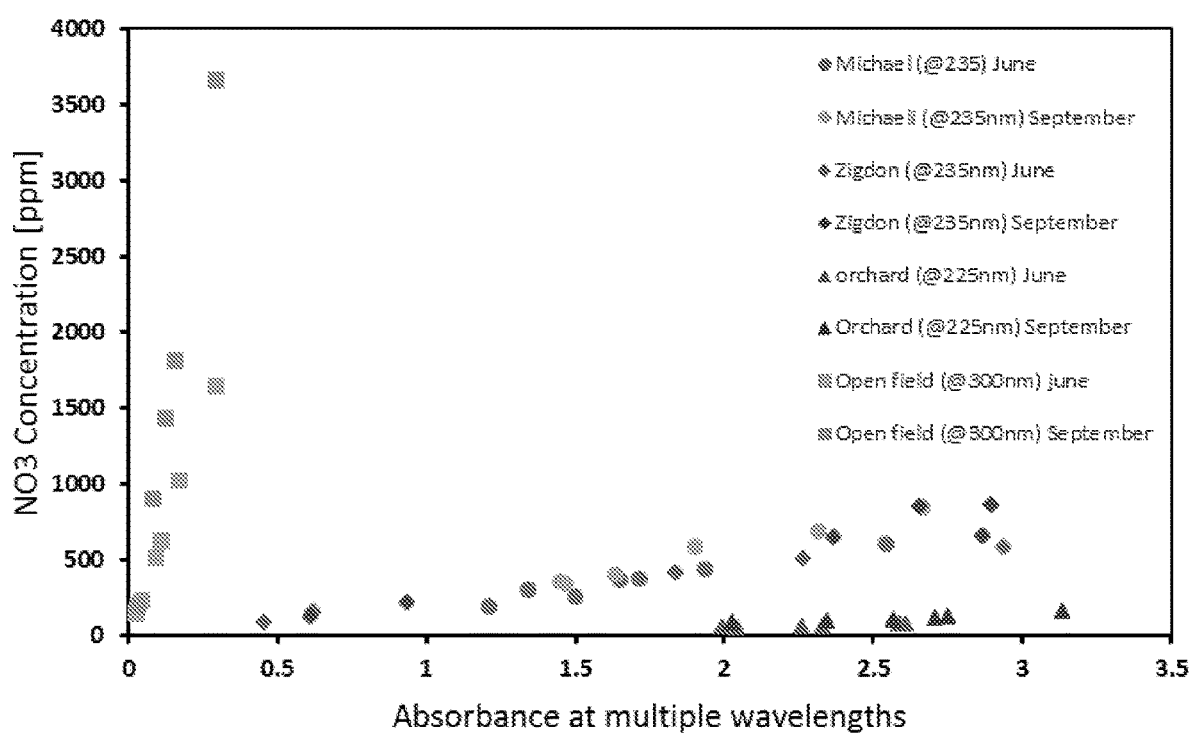
FIG. 12 is a graph confirming that the calibration eguation remains stable with the passage of time.

Moreover, a second field sampling tour, held three months from the time of the initial calibration, had confirmed that the calibration equation remains stable with the passage of time, as indicated by the results shown in FIG. 12.

Example 4

A Two-Step Procedure for Choosing a Wavelength for Spectral Analysis and Generation of a Calibration Curve This example demonstrates a procedure for screening a wavelength range to determine which wavelength is most suitable for spectral analysis of nitrate.

Samples of porewater were taken from an agricultural land. In the study reported herein, due to large variation of the natural nitrate concentration across the field, it was possible to create a single, satisfactory calibration curve following the initial sampling of the field under study (that is, there was no need for further spiking/diluting the raw samples in order to expand the concentration range). The so-formed single calibration curve is applicable for all individual monitoring units distributed in the field.

First, nitrate concentration of each sample was determined using 'DIONEX ICS 5000' ion chromatograph. Next, absorbance intensity of each sample was measured versus wavelength, across a range of 190 to 360 nm. Then the wavelengths are screened to satisfy two requirements.

First requirement (R-squared test): the strength of the correlation between the two variables, that is, how strong there is a linear relationship between the two sets of data (the known nitrate concentrations and corresponding absorbance intensities measured at each wavelength) is estimated using the R-squared parameter. That is, the R-squared is calculated and plotted versus wavelength. Wavelengths showing R-squared below a certain threshold are rejected, while the remaining wavelengths displaying R-squared above the threshold are used to form a set of candidate wavelength.

Figure 13:
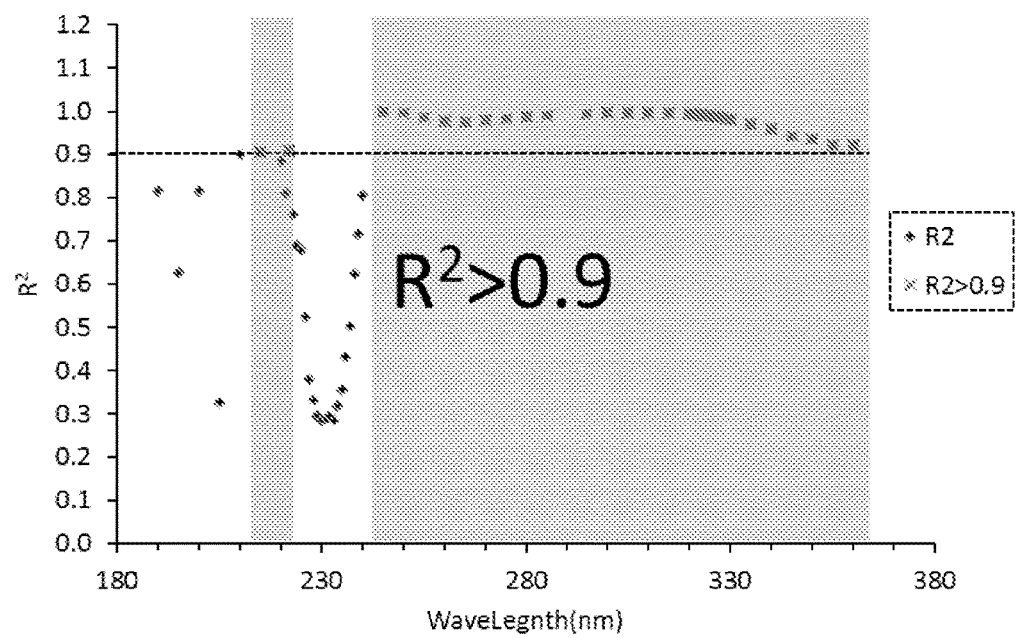
FIG. 13 illustrates the first step of a screening procedure described herein.

FIG. 13 illustrates the first step of the screening procedure outlined above, with R-squared value of 0.9 being applied as a threshold value. Each data point in FIG. 13 represents the correlation strength as R-Squared between a known set of nitrate concentration and absorbance intensity values. Data sets having R-Square values lower than $R^2 > 0.9$ are filtered out. The remaining data points, marked as red crosses on in the graph of FIG. 13, show good potential for generating a calibration equation. For example, it is seen from the R-squared versus wavelength plot of FIG. 13 that $\lambda = 245$ nm and $\lambda = 300$ nm meet the $R^2 > 0.9$ requirement ($R^2_{\lambda=245\ nm} = 0.9988$ and $R^2_{\lambda=300\ nm} = 0.9999$).

Figure 14:
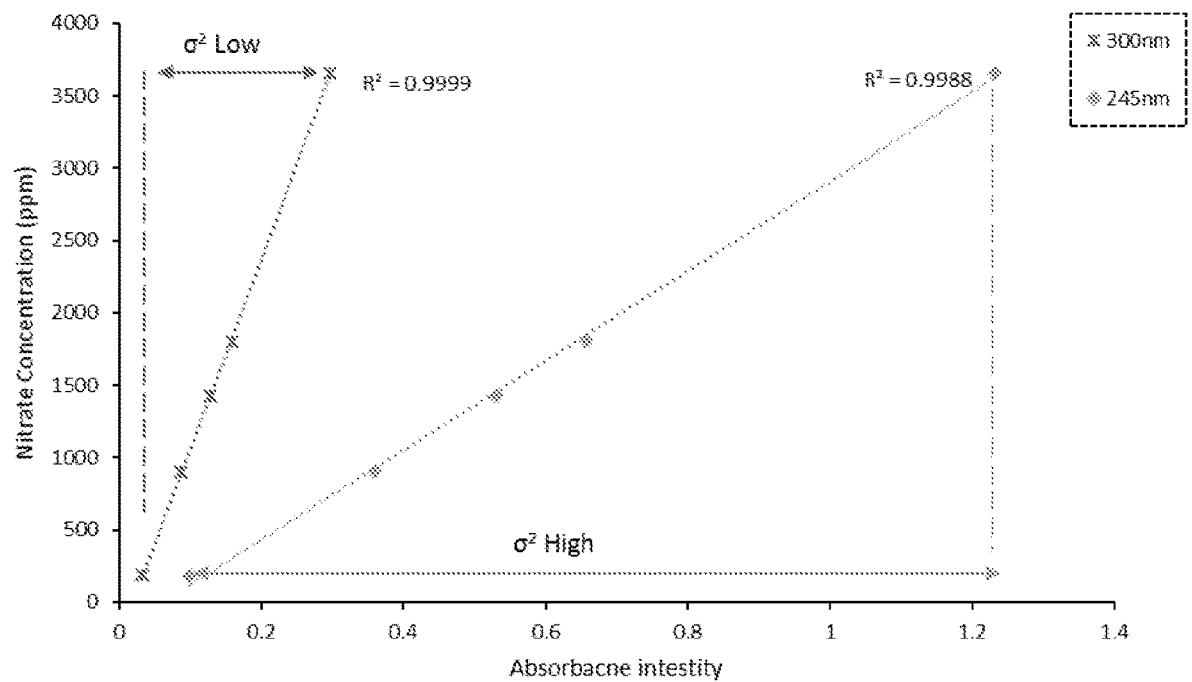
FIG. 14 demonstrates the two calibration curves made at 245nm and 300nm.

Second requirement (variance test): FIG. 14 demonstrates the two calibration curves made at 245 nm and 300 nm (marked by rhombuses and crosses, respectively). It is seen that the calibration curve at 300 nm has lower variance than 245 nm, and as such is more sensitive to measurement error. Thus, slights variations in the absorbance intensity values will result in much higher changes in measured value.

Figure 15:
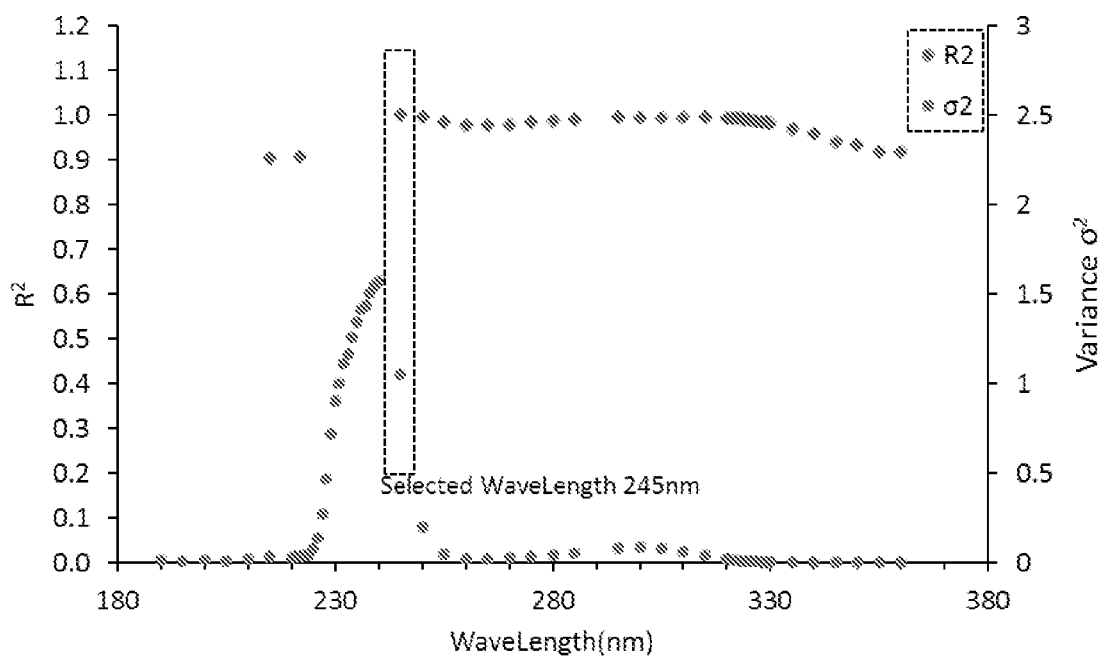
FIG. 15 is a graph showing that it is $\lambda=245$nm which emerges as the most suitable wavelength for spectral analysis for measuring nitrate concentration in the field under consideration.

Thus, as illustrated in FIG. 15, where both $R^2$ (left ordinate, marked by rhombuses) and $\sigma^2$ (right ordinate, marked by circles) are plotted versus wavelength, it is $\lambda = 245$ nm which emerges as the most suitable wavelength for spectral analysis for measuring nitrate concentration in the field under consideration.

The invention claimed is:

1. A system for measuring with the aid of light absorption spectrometry the concentration of one or more analytes in porewater in soil, the system comprising:
   one or more monitoring unit(s), each monitoring unit comprising a porewater sampler, an optical flow cell with a tube connecting the liquid inlet port of said optical flow cell to said porewater sampler; and vacuum arrangement to enable extraction of porewater, said vacuum arrangement comprising a sampling cell charged with vacuum, with a tube connecting the optical flow cell's outlet port to the sampling cell;
   at least one light source for generating a light beam to be transmitted through said optical flow cell; and
   at least one detector for obtaining spectral information from the beam exiting said optical flow cell.

2. A system according to claim 1, comprising:
   one or more monitoring unit(s), each monitoring unit consisting of a porewater sampler, an optical flow cell and a sampling cell, with tubes connecting the liquid inlet and outlet ports of said optical flow cell to said porewater sampler and sampling cell, respectively;
   a vacuum generating device to enable extraction of porewater, said device being a vacuum pump for charging the sampling cell with vacuum;
   at least one light source for generating a light beam to be transmitted through said optical flow cell; and
   at least one detector for obtaining spectral information from the beam exiting said optical flow cell.

3. A system according to claim 1, comprising an array of individual monitoring units installed at different locations across a field to create a network of sampling points in said field.

4. A system according to claim 3, wherein the system comprises a single light source and a single detector.

5. A system according to claim 4, further comprising a mechanical control unit to divert the light beam generated by said single light source between the optical flow cells of the individual monitoring units, wherein the mechanical control unit comprises fiber optic multiplexer.

6. A system according to claim 1, comprising an array of individual monitoring units installed along a borehole with the aid of a sleeve inserted into the borehole and filled to achieve tight contact to the wall of the borehole, to create a network of sampling points along said borehole.

7. A system according to claim 6, comprising a single light source and a single detector.

8. A system according to claim 6, wherein the optical flow cell has a front face through which a light beam travelling from the light source via an illumination optical fiber enters said optical flow cell, and a rear face through which a light beam exiting the optical flow cell is guided via a sample optical fiber to the detector, wherein the optical flow cell is provided with an optical arrangement comprising at least one of the following:
   one or more lenses mounted in the front side and/or one or more lenses mounted in the rear side of said optical flow cell;
   one or more deflectors and/or mirrors mounted in the front side and/or one or more deflectors and/or mirrors mounted in the rear side of said optical flow cell;
   wherein the optical arrangement is configured to focus the light beam traveling via the illumination optical fiber onto said optical flow cell, and/or to reflect light beam exiting said optical flow cell back to the said optical flow cell;
   and wherein the system further optionally comprises one or more of spatial light modulator and/or modulators at the output of said illumination fiber or inlet of said sample fiber, wherein each optical flow cell is associated with a specific code or frequency; the system further comprising a controller and a computer to assign each monitoring unit with said code or frequency.

9. A system according to claim 1, wherein the porewater sampler comprises a porous interface in the form of a lateral surface of a cylinder designed to have a minimal inner dead volume or an elongated body bounded by a porous lateral surface with a spacer disposed within the interior defined by said lateral surface, said spacer occupying at least 90% of the volume of said interior space.

10. A system according to claim 9, wherein the porewater sampler comprises a pipe bounded by a lateral surface made of porous ceramic material and a cylindrical spacer coaxially positioned within said pipe.

11. A system according to claim 1, wherein tube connecting the liquid inlet port of the optical flow cell to the porewater sampler is made of chemically resistant plastic with inner diameter from 1.0 to 2.0 mm.

12. A system according to claim 11, wherein the volume of the cavity in the optical flow cell is from 1 to 2 ml.

13. A method of quantitative in-situ and real time monitoring with the aid of light absorption spectrometry of one or more analytes in porewater, the method comprising:
extracting porewater from soil using a porewater sampler, to produce a porewater stream;
directing said porewater stream into an optical flow cell;
transmitting light beam across the porewater stream flowing through the optical flow cell;
obtaining spectral information from the beam exiting the optical flow cell to determine the concentration of one or more analytes in the porewater with the aid of a first calibration curve constructed at a first selected wavelength suitable for the chemical composition of the soil and concentration range of said analyte; and
switching to a second calibration curve constructed at a different wavelength if the concentration measured is not within said concentration range associated with said first calibration curve.

14. A method according to claim 13, comprising discharging the porewater stream to a sampling cell to enable collection of samples.

15. A method according to claim 13, wherein the method is for multi-point measurements across a field from a plurality of sampling points, each point equipped with a monitoring unit consisting of porewater sampler, an optical flow cell and optionally a sampling cell.

16. A method according to claim 15, wherein the first and second calibration curves are chosen from a preset library of calibration curves generated by obtaining raw samples from one or more sampling points in the field, following which the raw samples are optionally spiked and diluted, to create a low and high concentration ranges solutions which are used to form calibration curves adoptable for the chemical composition of the porewater in each individual sampling point.

17. A method according to claim 16, wherein the wavelength at which a calibration curve is created is determined by a procedure comprising the steps of:
A) obtaining a set of samples $S_i$ $\{S_1, S_2, S_3, \ldots, S_i, \ldots, S_n\}$,
B) determining concentrations $C_i$ ($C_1, C_2, C_3, \ldots, C_i, \ldots, C_n$) of said samples;
C) measuring the absorbance intensity versus wavelength across a predetermined range spanning the $\lambda_1$ to $\lambda_{final}$ region for each sample $S_i$ ($1 \le i \le n$), to ascribe to each sample $S_i$ a set of absorbance readings A(i) ($1 \le i \le n$): $A(i)\{A(i))_{\lambda_1}, A(i)_{\lambda_2}, A(i))_{\lambda_3} \ldots A(i)_{\lambda_k}, \ldots A(i)\lambda_{final}\}$, wherein $A(i))_{\lambda_k}$ indicates the absorbance intensity measured for sample Si at a specific wavelength $\lambda_k$,
D) determining optimal wavelength $\lambda_o$ for calibration, by searching for a set of data consisting of $A(i)\lambda_o$ ($1 \le i \le n$) which fits the best to the set of data of known concentrations $C_i$ ($1 \le i \le n$).

18. A method according to claim 13, wherein the analyte is nitrate ion and the light beam is a light beam in the 190 to 850 nm region.

19. A device for detecting an analyte in a plurality of liquid samples with the aid of light spectrometry, wherein the device comprises at least one light source, a plurality of sample holders and at least one detector, wherein each sample holder has a front face through which a light beam travelling from the light source via a wave guide enters said sample holder, and a rear face through which a light beam exiting the sample holder is guided to the detector, wherein an optical flow cell is used as the sample holder, the optical flow cell being provided with an optical arrangement comprising at least one of the following:
one or more lenses mounted in the front side and/or one or more lenses mounted in the rear side of said sample holder;
one or more deflectors and/or mirrors mounted in the front side and/or one or more deflectors and/or mirrors mounted in the rear side of said sample holder;
wherein the optical arrangement is configured to focus the light beam traveling from the light source onto said sample holder; to reflect light beam exiting said sample holder back to said sample holder;
and wherein the system further comprises one or more of spatial light modulator and/or modulators wherein each sample holder is associated with a specific code or frequency;
the device further comprising a controller connected to a computer to assign each sample holder with said code or frequency.

* * * * *